US006472153B1

(12) United States Patent
Dempcy et al.

(10) Patent No.: US 6,472,153 B1
(45) Date of Patent: Oct. 29, 2002

(54) HYBRIDIZATION-TRIGGERED FLUORESCENT DETECTION OF NUCLEIC ACIDS

(75) Inventors: Robert O. Dempcy, Bellevue, WA (US); Irina Aleksandrovna Afonina, Mill Creek, WA (US); Nicolaas M. J. Vermeulen, Woodinville, WA (US)

(73) Assignee: Epoch Biosciences, Inc., Bothell, WA (US)

( * ) Notice: Subject to any disclaimer, the term of this patent is extended or adjusted under 35 U.S.C. 154(b) by 0 days.

(21) Appl. No.: 09/428,236

(22) Filed: Oct. 26, 1999

(51) Int. Cl.[7] .................. C12Q 1/68; C07H 19/00; C07H 21/00; C07H 21/02; C07H 21/04
(52) U.S. Cl. .................. 435/6; 536/22.1; 536/23.1; 536/24.3; 536/24.33; 536/25.3; 536/25.32; 536/26.6
(58) Field of Search .................. 435/6; 536/22.1, 536/23.1, 24.3, 24.33, 25.3, 25.32, 26.6

(56) References Cited

U.S. PATENT DOCUMENTS

| | | | |
|---|---|---|---|
| 5,124,246 A | 6/1992 | Urdea et al. | 435/6 |
| 5,237,101 A | 8/1993 | Nicolaou et al. | 568/28 |
| 5,446,137 A | 8/1995 | Maag et al. | 514/44 |
| 5,594,118 A | 1/1997 | Urdea et al. | 536/23.1 |
| 5,871,908 A | 2/1999 | Henco et al. | 435/6 |
| 5,902,724 A | 5/1999 | Lane et al. | 435/6 |
| 6,072,046 A | * 6/2000 | Reed et al. | 536/23.1 |

FOREIGN PATENT DOCUMENTS

| | | |
|---|---|---|
| EP | 0231495 B1 | 12/1986 |
| EP | 0231495 | 12/1986 |

OTHER PUBLICATIONS

Stratagene Catalog. p. 39, 1988.*
Ishiguro et al., *Fluorescence Detection of Specific Sequence of Nucleic Acids by Oxazole Yellow–Linked Oligonucleotides. Homogeneous Quantitative Monitoring of in vitro Transcription,* Nucleic Acids Research, (1996) vol. 24, No. 24, 4992–4997.
Inoue et al.,*Fluorescence Property of Oxazole Yellow–Linked Oligonucleotide. Triple Helix Formation and Photocleavage of Double–Stranded DNA in the Presence of Spermine* , Bioorganic & Medicinal Chemistry 7 (1999) 1207–1211.
Zimmer and Wahnert, *Nonintercalating DNA–Binding Ligands: Specificity of the Interaction and Their Use As Tools in Biophysical, Biochemical and Biological Investigations of the Genetic Material,* Prog. Biophys., Moloch., Biol., (1986) vol. 47, 31–112.
Loontien's et al., *Binding of Heochst 33258 and 4', 6–Diamidino–2–Phenylindole to Self–Complementary Decadeoxynucleotides With Modified Exocyclic Base Substitutes,* Biochemistry (1991) 30, 182–189.

(List continued on next page.)

*Primary Examiner*—Jezia Riley
(74) *Attorney, Agent, or Firm*—Townsend and Townsend and Crew LLP

(57) ABSTRACT

Compositions and methods for fluorescent detection of nucleic acids are provided. The compositions can be detected by fluorescence when hybridized to a nucleic acid containing a target sequence, but are non-fluorescent in the non-hybridized state. Alternatively, the fluorescence properties of the compositions change in a detectable manner upon hybridization to a nucleic acid containing a target sequence. Methods for synthesis and methods of use of the compositions are also provided.

45 Claims, 9 Drawing Sheets

OTHER PUBLICATIONS

Conway and McLaughlin, *The Covalent Attachment of Multiple Fluorophores to DNA Containing Phosphorothioate Diesters Results in Highly Sensitive Detection of Single–Stranded DNA*, Bioconjugate Chem. (1991) 452–457.

Patel et al., *Thermodynamics of Interaction of a Fluorescent DNA Oligomer With the Anti–Tumor Drug Netropsin*, Eur. J. Biochem (1992) Feb. 1; 203(3) 361–366.

O'Donnell et al., *Synthesis and Properties of a Hoechst–Like Minor–Groove Binding Agent Tethered to an Oligoodeoxynucleotide*, Bioorganic & Medicinal Chemistry (1995) Jun. 3(6) 743–750.

Harapanhalli et al., *[$^{-125}$I/$^{127}$I]IodoHoechst 33342: Synthesis, DNA Binding, and Biodistribution*, J. Med. Chem. (1996) 39, 4804–9.

Rye et al., *High–Sensitivity Two–Color Detection of Double–Stranded DNA With a Confocal Fluorescence Gel Scanner Using Ethidium Homodimer and Thiazole Orange*, Nucleic Acids Research, (1990) vol. 19, No. 2, 327.

Jocobson et al., *Site Selective Bis–Intercalation of a Homodimeric Thiazole Orange Dye in DNA Oligonucleotides*, Nucleic Acids Research (1995) vol. 23, No. 5, 753–760.

Spielmann et al., *Solution Structure of the DNA Complex With the Fluorescent Bis–Intercalator TOTO Determined by NMR Spectroscopy*, Biochemistry (1995) 34, 8542–53.

Hansen et al., *Bis–Intercalation of a Homodimeric Thiazole Orange Dye in DNA in Symmetrical Pyrimidine—Pyrimidine–Purine–Purine Oligonucleotides*, Nucleic Acids Research (1996) vol., 24, No. 5, 859–867.

Peterson and Jocobsen, *Solution Structure of a DNA Complex with the Fluorescent Bis–Intercalcator TOTO Modified on the Benzothiazole Ring*, Bioconjugate Chem. (1998) 9, 331–40.

Wiederholt et al., *Oligonucleotides Tethering Hoechst 33258 Derivatives: Effect of the Conjugation Site on Duplex Stabilization and Fluorescence Properties;* Bioconjugate Chem. (1997) 8, 119–126.

Wiederholt et al., *DNA–Tethered Hoechst Groove–Binding Agents: Duplex Stabilization and Fluorescence Chracteristics*, J. Am. Chem. Soc. (1996) 118, 7055–7062.

Bailly and Henichart DNA Recognition By Intercalator–Minor–Groove Binder Hybrid Molecules, Bioconjugate Chemistry (1991) vol. 2, No. 6, 379–93.

Levina et al., *Conjugates of Minor Groove DNA Binders with Oligodeoxynucleotides: Synthesis and Properties*, Antisense & Nucleic Acid Drug Development (1996) 6:75–85.

Federico Gago, *Stacking Interactions and Intercalative DNA Binding*, A Companion to Methods in Enzymology (1998) 14, 277–292.

Peter E. Nielsen, *Applications of Peptide Nucleic Acids*, Current Opinion in Biotechology (1999) 10: 71–75.

Koch et al., *PNA–Peptide Chimerae[1]*, Tetrahedron Letters (1995) vol. 36, No. 38, 6933–6936.

Lampe et al., *Factors Influencing the Extent and Selectivity of Alkylation Within Triplexes by Reactive G/A Motif Oligonucleotides*, Nucleic Acids Research (1997) vol. 25, No. 20, 4123–4131.

Ornstein and Fresco, *Correlation of Crystallographically Determined and Computationally Predicted Hydrogen–Bonded Pairing Configurations of Nucleic Acid Bases*, Proc. Natl. Acad. Sci USA, (1983) vol. 80, 5171–5175.

Kumar et al., *Solution Structure of a Highly Stable DNA Duplex Conjugated to a Minor Groove Binder*, Nucleic Acids Research (1998) vol. 26, No. 3, 831–838.

Casas–Finet et al., *Structural Basis for the Nucleic Acid Binding Cooperativity of Bacteriophage T4 Gene 32 Protein: The $(Lys/Arg)_3(Ser/Thr)_2(LAST)$ Motif.* Proc. Natl. Acad. Sci. USA (1992) vol. 89, 1050–54.

Boger et al., *Studies on the Total Synthesis of CF–1065: Preparation of a Synthetic, Simplified 3–Carbamoyl–1–2–dihydro–3H–Pyrrolo[3,2–e]indole Dimer/Trimer/Tetramer (CDPI Dimer/Trimer/Tetramer) and Development of Methodology for PDE–I Dimer Methyl Ester Formation*, J. Org. Chem. (1987) 52, 1521–1530.

\* cited by examiner

HYBRIDIZATION-TRIGGERED FLUORESCENT DETECTION OF NUCLEIC ACIDS

CROSS-REFERENCE TO RELATED APPLICATIONS

Not applicable.

STATEMENT OF RIGHTS TO INVENTIONS MADE UNDER FEDERALLY SPONSORED RESEARCH

Not applicable.

TECHNICAL FIELD

The present invention is in the field of molecular biology. More specifically, the invention is in the field of assays that utilize fluorescently-labeled probes and primers in hybridization assays for detection of nucleic acids.

BACKGROUND

The use of fluorescent molecules in the biological sciences for research and diagnostic purposes is well known. See, for example, Kirkbright "Fluorescent Indicators" in Indicators, (ed. Bishop, E.) Pergamon Press, New York, Chapter 9, pp. 685–708, 1972; and Haugland (1996) *Handbook of Fluorescent Probes and Research Chemicals*, Sixth edition, Molecular Probes, Inc., Eugene, Oreg. Fluorescent moieties have been used for non-specific labeling of single- and double-stranded nucleic acids (e.g., acridine, ethidium bromide) and for labeling of nucleic acid probes that are used in sequence-specific detection of nucleic acid targets. In general, when fluorescent nucleic acid binding molecules and/or fluorescently-labeled probes are used for nucleic acid detection, unbound fluorescent material must be removed from the system, prior to analysis, to maximize detection of a signal. If unbound material is not removed, background fluorescence leads to a reduction in the signal:noise ratio.

Compositions which are fluorescent when bound to double-stranded DNA, but which do not fluoresce (or fluoresce at a different wavelength) when unbound, have been described. See, for example, Haugland, supra, pp. 144–156 and 161–174, especially pp. 161–165. Although such compositions may exhibit fairly general sequence preferences (e.g., for AT-rich vs. GC-rich target sequences), they are not capable of either sequence-specific detection of a target or of mismatch discrimination between targets having related but non-identical sequences. In addition, such compositions cannot be used for multiplex detection of target sequences (i.e., simultaneous detection of more than one target sequence).

Several new analytical techniques depend on sequence-specific detection and mismatch discrimination using fluorescence as a readout. For instance, homogeneous detection methods for monitoring the accumulation of specific PCR products have recently been developed. One of these assays utilizes an oligonucleotide probe which contains a fluorescent molecule at its 5' end and a fluorescence quencher at its 3' end. Because of the presence of the quencher, the oligonucleotide probe does not exhibit fluorescence, or exhibits relatively low fluorescence, in the single-stranded state. The assay exploits the 5'→3' nuclease activity of Taq DNA polymerase to hydrolyze such a probe after it has formed a sequence-specific duplex with a target nucleic acid. Hydrolysis releases the fluorescent molecule from the 5' end of the probe, removing it from proximity with the quencher, thereby allowing increased fluorescence to occur. Lee et al. (1993) *Nucleic Acids Res.* 16:3761–3766. In another recently-developed technique, microvolume multi-sample fluorimeters with rapid temperature control have been developed for use with 5'-nuclease assays using double-labeled fluorescent probes. Wittwer et al. (1997) *Biotechniques* 22:176–181. U.S. Pat. No. 5,871,908 describes a homogeneous assay in which fluorescent signal varies with a temperature gradient and the variation is detected in real time. However, all of these assays involve post-hybridization detection steps, often involving the use of enzymes, which are costly, time-consuming and can be difficult to regulate, in terms of their activity.

There is thus a need for sensitive and straightforward methods and compositions for sequence-specific detection of nucleic acid targets; in particular fluorescent detection. Besides the advantages of using fluorescent molecules as an alternative to radioisotopes, improvements in speed, economy and convenience would attend the development of a method in which the hybridization event itself provided a direct readout, without requiring subsequent detection steps, such as enzymatic treatment of hybridized material.

Tyagi et al. (1996) *Nature Biotechnol* 14:303–308 described probes containing a fluorophore and a quencher molecule which, in the unhybridized state, form a hairpin which brings the fluorophore and the quencher into proximity so that fluorescence is quenched. Upon hybridization, the hairpin structure is disrupted and fluorescence is observed. Such probes require the attachment of both a fluorophore and a quencher, and also must contain regions of self-complementarity, which may interfere with their ability to hybridize to their target.

Minor groove binding agents that non-covalently bind within the minor groove of double stranded DNA have been described. Zimmer et al. (1986) *Prog. Biophys. Molec. Biol.* 47:31–112; Levina et al. (1996) *Antisense & NucL. Acid Drug Develop.* 6:75–85. Hybridization assays using an oligonucleotide coupled to a minor groove binder (MGB) have been described in U.S. Pat. No. 5,801,155, and in International Patent Application No. PCT/US99/07487. These publications describe the ability of minor groove binders, when conjugated to an oligonucleotide, to increase the ability of the oligonucleotide to distinguish between a perfectly-matched target sequence and a target sequence with a single-nucleotide mismatch. This heightened discriminatory ability of MGB-oligonucleotide conjugates is reflected in a greater difference in melting temperature ($T_m$) between matched and mismatched duplexes formed with an MGB-oligonucleotide conjugate, on the one hand, and matched and mismatched duplexes formed with an unmodified oligonucleotide, on the other. The aforementioned U.S. Pat. No. 5,801,155, and International Patent Application No. PCT/US99/07487 additionally disclose that a duplex comprising a MGB-oligonucleotide conjugate has a higher melting temperature than a duplex of identical sequence comprising an unmodified oligonucleotide. This property of duplexes comprising a MGB-oligonucleotide conjugate allows more facile detection of related mismatched sequences with a MGB-oligonucleotide probe, and enables the use of shorter oligonucleotide probes in PCR amplification reactions, if the probe is conjugated to a MGB. These publications also describe the use of an oligonucleotide coupled to a minor groove binder, a fluorophore and a fluorescent quencher, in hydrolyzable probe assays.

Intercalating agents are, generally speaking, flat aromatic molecules that bind non-covalently to double-stranded DNA or RNA by positioning themselves between adjacent base pairs of the duplex. Gago (1998) *Method* 14:277–292. U.S. Pat. No. 4,835,283 and PCT publication WO 98/50541, for example, disclose oligonucleotides that are covalently bound to an intercalating group. Oligonucleotides conjugated to either minor groove binders or intercalating groups can be used in hybridization assays.

Hoechst 33258 and 33342 are examples of fluorescent dyes that bind in the minor groove of DNA duplexes. A conjugate consisting of an oligonucleotide coupled to a Hoechst-like minor groove binder has been observed to show increased fluorescence upon hybridization to a single-stranded target. O'Donnell et al. (1995) *Biorg. Med. Chem.* 3:743–750; and Wiederholt et al. (1996) *J. Amer. Chem. Soc.* 118:7055–7062. This conjugate consisted solely of an oligonucleotide bound to a MGB.

EP 231 495 discloses a polynucleotide compound comprising at least two entities, which upon hybridization is capable of generating a change in property of the hybrid.

SUMMARY OF THE INVENTION

The present invention provides methods and compositions for improved hybridization detection and mismatch discrimination by fluorescence. In the practice of the invention, an increase in fluorescent signal, a change in fluorescence excitation and/or emission, and/or some other change in fluorescence properties occurs after hybridization of an oligonucleotide, appropriately labeled with a latent fluorophore and a minor groove binder, to a complementary target.

In one aspect, the present invention encompasses a covalently bound oligonucleotide (ODN)/minor groove binder (MGB)/latent fluorophore (LF) combination. The oligonucleotide comprises a plurality of nucleotides (and/or modified nucleotides and/or nucleotide analogues), a 3' end and a 5' end. A minor groove binder moiety is a radical of a molecule having a molecular weight of approximately 150 to approximately 5000 Daltons which molecule binds in a non-intercalating manner into the minor groove of non-single-stranded nucleic acids or hybrids, analogues and chimeras thereof (i.e., double- or triple-stranded polynucleotides) with an association constant greater than approximately $10^3 M^{-1}$. The minor groove binder moiety is covalently attached at the 3' end and/or the 5' end, and/or to at least one of said nucleotides, modified nucleotides and/or nucleotide analogues of the oligonucleotide, and is typically attached to the oligonucleotide through a first linking group having a backbone length of no more than about 100 atoms. A latent fluorophore is a radical of a molecule having a molecular weight of approximately 150 to approximately 5000 Daltons which binds in an intercalating manner into non-single-stranded nucleic acids or hybrids, analogues and chimeras thereof, or lies preferentially in the minor groove, or in another manner is oriented to the DNA molecule by the minor groove binder moiety so that it becomes fluorescent or its fluorescence properties are changed in a detectable way. Typically, the latent fluorophore is attached to the minor groove binder moiety through a second linking group having a backbone length of no more than about 50 atoms.

In one embodiment, the ODN-MGB-LF conjugate is relatively non-fluorescent in its single-stranded state, but becomes fluorescent after hybridization to a target sequence. In another embodiment, the ODN-MGB-LF conjugate may exhibit some fluorescence emission at one or more particular wavelengths in its single-stranded state, but, after hybridization, its maximal fluorescence emission is shifted to a different wavelength. In yet another embodiment, the wavelength at which maximal fluorescence excitation occurs can change after hybridization of an ODN-MGB-LF conjugate.

In another aspect, the present invention encompasses processes for the synthesis of covalently-bound oligonucleotide-minor groove binder-latent fluorophore conjugates. The invention also provides novel compositions for use in the synthesis of ODN-MGB-LF conjugates.

In yet another aspect, the invention relates to the use of compositions comprising an oligonucleotide, a minor groove binder and a latent fluorophore, in covalent or functional linkage, as hybridization probes for fluorescent detection in analytical and diagnostic methods. These methods include but are not limited to, PCR (including real-time PCR), single nucleotide mismatch discrimination, target amplification, signal amplification and assays utilizing oligonucleotide arrays.

In an exemplary method for detecting a target sequence in a polynucleotide, an ODN-MGB-LF conjugate is combined with a sample containing a polynucleotide to form a hybridization mixture, wherein the ODN portion of the conjugate comprises a sequence which hybridizes to the target sequence, the hybridization mixture is incubated under conditions which yield specific hybridization, and thereafter fluorescence of the hybridization mixture is measured, wherein fluorescence is indicative of the presence of the target sequence.

In another embodiment, the compositions and methods of the invention are used for detection of a target sequence in a polynucleotide, wherein the polynucleotide is in a sample comprising a plurality of polynucleotides having different sequences.

In yet another embodiment, the compositions and methods of the invention are used for detection of a target sequence in a polynucleotide, wherein the polynucleotide is present in a mixture of other polynucleotides, and wherein one or more of the other polynucleotides in the mixture comprise sequences that are related but not identical to the target sequence. In this embodiment, an ODN-MGB-LF conjugate is contacted with the aforementioned mixture of polynucleotides, wherein the ODN-MGB-LF forms a stable hybrid only with a target sequence that is perfectly complementary to the oligonucleotide portion of the composition and wherein the composition does not form a stable hybrid with any of the related sequences. After hybridization, the fluorescence of the mixture is measured, wherein fluorescence is indicative of the presence of the target sequence.

In a further embodiment, the compositions and methods of the invention are used for single-nucleotide mismatch discrimination.

In one embodiment, the compositions are used for the detection of single-stranded nucleic acids. The ODN portion of the ODN-MGB-LF conjugate forms a duplex with a single-stranded target nucleic acid, and interactions of the MGB and LF portions of the conjugate with the resulting duplex nucleic acid result in enhanced fluorescence, or some other change in the fluorescence properties of the latent fluorophore.

In another embodiment, the compositions of the invention are used for detection of double-stranded nucleic acid targets. In this case the ODN portion of the conjugate is a triplex-forming oligonucleotide. See, for example, Fresco, U.S. Pat. No. 5,422,251; Hogan, U.S. Pat. No. 5,176,996; and Lampe (1997) *Nucleic Acids Res.* 25:4123–4131. Formation of a triplex between the conjugate and a double-stranded target results in enhanced fluorescence, or some other change in the fluorescence properties of the latent fluorophore.

In another embodiment, the invention provides compositions and methods for the simultaneous detection of multiple target sequences in a sample (i.e., multiplex detection).

In another embodiment, the invention provides compositions and methods for amplification of a target sequence, wherein the amplification primer(s) are capable of hybridization-triggered fluorescence. This embodiment is particularly suitable for various amplification methods in which the product is detectable in real time.

In further aspects, ODN-MGB-LF conjugates are immobilized on a solid support, preferably in an ordered array. An immobilized conjugate can be used for capture of a target polynucleotide and/or as a primer using a captured polynucleotide as a template. In these and other applications, the compositions of the invention are able to discriminate between closely related polynucleotide sequences.

In another aspect, the invention provides kits for fluorescent detection of nucleic acids, and for mismatch discrimination between related nucleic acids, wherein the kits comprise at least one ODN-MGB-LF conjugate.

BRIEF DESCRIPTION OF THE DRAWINGS

FIG. 1. Schematic representations of ground ($S_0$) and excited singlet ($S_1$) states for an exemplary cyanine dye.

FIG. 2. Fluorescence of single- and double-stranded thiazole orange-minor groove binder-oligonucleotide conjugates.

FIG. 3. Effect of a minor groove binder on hybridization-triggered fluorescence.

FIG. 4. Hybridization-triggered fluorescence in a DNA-RNA hybrid.

MODES FOR CARRYING OUT THE INVENTION

Figure 1A:
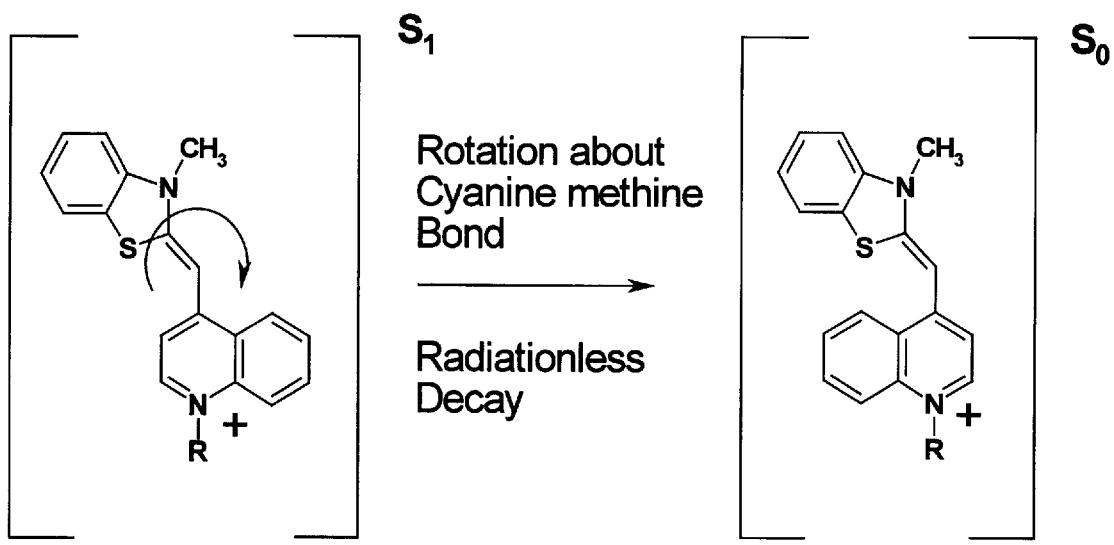
FIG. 1A depicts radiationless decay by free dye.

This invention is directed to the concept of hybridization-triggered fluorescence detection of nucleic acids and provides the basis for a new class of diagnostic probes for detection and mismatch discrimination of specific DNA and/or RNA sequences.

The basic constructs of the invention involve covalent conjugates of an oligonucleotide, a minor groove binder and a potentially fluorogenic reporter group. In one configuration, conjugates of the invention have the structure ODN-MGB-LF. These can constitute an essentially linear arrangement of the ODN, MGB and LF components such that a MGB has an ODN attached to one end and a LF to the other, or an arrangement in which an ODN and a LF are attached to the same end of a MGB. In another configuration, the conjugates of the invention have a fluorogenic reporter group covalently interposed between an oligonucleotide and a minor groove binder, to give a structure which can be represented ODN-LF-MGB.

The fluorogenic reporter group is chosen such that hybridization of the oligonucleotide to a complementary target sequence results in an enhancement, at a particular wavelength, in the fluorescence quantum yield of the fluorogenic reporter group. Accordingly, the fluorogenic reporter group is also known as a latent fluorophore (LF). Enhancement in fluorescence intensity can result from binding of the reporter group to the hybrid formed between the oligonucleotide and the target sequence, from a particular positioning of the reporter group with respect to the hybrid thus changing the environment of the fluorogenic reporter, from intercalation of the reporter group into the hybrid, and/or from restriction of rotational movement of the fluorogenic compound as a result of hybridization.

For the purposes of the invention, hybridization includes interaction of an oligonucleotide with a single-stranded nucleic acid to form a duplex, as well as interaction of an oligonucleotide with a double-stranded nucleic acid to form a triplex. For detection of double-stranded nucleic acid targets, the oligonucleotide portion of the composition is a triplex-forming oligonucleotide. Design of triplex forming oligonucleotides, based on non-Watson-Crick base-pairing schemes, such as Hoogsteen and reverse Hoogsteen base pairing, is well-known to those of skill in the art. See, for example, Fresco, supra; Hogan, supra; Lampe, supra; and Omstein et al. (1983) *Proc. Natl. Acad. Sci. USA* 80:5171–5175. For detection of a duplex target, a triplex-forming oligonucleotide is linked to a MGB through an appropriate linker having a backbone of approximately 100 atoms (Kutyavin et al. (1997) *Nucleic Acids Res.* 25:3718–3723), and the MGB is in turn linked to a latent fluorophore through a linker of approximately 50 atoms preferebly 40 atoms, more preferably 30 atoms, more preferably 20 atoms, still more preferably 10 atoms and most preferably 5–6 atoms.

The invention provides selected latent fluorophore-MGB-oligonucleotide conjugates which exhibit increased fluorescence upon hybridization, compared to the latent fluorophore-MGB-oligonucleotide conjugate alone. The invention thus combines the enhanced hybrid stability and mismatch discrimination obtained with MGB-oligonucleotide conjugates (see, for example, U.S. Pat. No. 5,801,155, and International Patent Application No. PCT/US99/07487) with the speed, simplicity and sensitivity of detection by hybridization-triggered fluorescence.

The practice of the invention will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987 and annual updates); Gait (ed.), OLIGONUCLEOTIDE SYNTHESIS: A PRACTICAL APPROACH, IRL Press (1984); Eckstein (ed.), OLIGONUCLEOTIDES AND ANALOGUES: A PRACTICAL APPROACH, IRL Press (1991).

The disclosures of all publications and patents cited herein are hereby incorporated by reference in their entirety.

Oligonucleotides

Broadly speaking, the oligonucleotide portion of an ODN-MGB-LF conjugate comprises approximately 3 to 100 nucleotide units. However, longer oligonucleotides are also encompassed by the invention, and the term oligonucleotide is not intended to be limiting with respect to the length of the molecule to which the term refers. The nucleotide units which are incorporated into the ODNs in accordance with the present invention include the major heterocyclic bases naturally found in nucleic acids (uracil, cytosine, thymine, adenine and guanine) as well as naturally-occurring and synthetic modifications and analogues of these bases such as, for example, hypoxanthine, 2-aminoadenine, 2-thiouracil, 2-thiothymine, 5-$N^4$ ethenocytosine, 4-aminopyrrazolo[3,4-d]pyrimidine and 6-amino-4-hydroxy-[3,4-d]pyrimidine. Any modified nucleotide or nucleotide analogue compatible with hybridization of the ODN-MGB-LF conjugate to a target sequence is useful in the practice of the invention, even if the modified nucleotide or nucleotide analogue itself does not participate in base-pairing, or has altered base-pairing properties compared to naturally-occurring nucleotides.

The sugar or glycoside portion of the ODN portion of the conjugates can comprise deoxyribose, ribose, 2-fluororibose, and/or 2-O-alkyl or alkenylribose wherein the alkyl group comprises 1 to 6 carbon atoms and the alkenyl group comprises 2 to 6 carbon atoms. In the naturally-occurring nucleotides, modified nucleotides and nucleotide analogues that can comprise an ODN, the sugar moiety forms a furanose ring, the glycosidic linkage is of the β configuration, the purine bases are attached to the sugar moiety via the purine 9-position, the pyrimidines via the pyrimidine 1-position and the pyrazolopyrimidines via the pyrazolopyrimidine 1-position (which is equivalent to the purine 9-position). In a preferred embodiment, the sugar moiety is 2-deoxyribose; however, any sugar moiety known to those of skill in the art, that is compatible with the ability of the oligonucleotide portion of the compositions of the invention to hybridize to a target sequence, can be used.

In one embodiment, the nucleoside units of the ODN portion of the conjugate are linked by a phosphodiester backbone, as is well known in the art. In additional embodiments, internucleoside linkages can include any linkage known to one of skill in the art that is compatible with specific hybridization of the ODN including, but not limited to phosphorothioate, methylphosphonate, sulfamate (e.g., U.S. Pat. No. 5,470,967) and polyamide (i e., peptide nucleic acids). Peptide nucleic acids are described in Nielsen et al. (1991) *Science* 254: 1497–1500; U.S. Pat. No. 5,714,331; and Nielsen (1999) *Curr.Opin. Biotechnol.* 10:71–75. Thus, for example, part or all of the ODN portion of the conjugate can be a peptide (polyamide) nucleic acid (PNA).

In certain embodiments, the ODN portion of the conjugate can be a chimeric molecule; i.e., the ODN can comprise more than one type of base or sugar subunit, and/or the linkages can be of more than one type within the same ODN. For example, the ODN can be a PNA/DNA chimera. See, for example, Nielsen (1999) supra; and Koch et al. (1995) *Tetrahedron Letts.* 36:6933–6936. In addition, the ODN can be interrupted by non-nucleotide components.

The ODN portion of the ODN-MGB-LF conjugates can comprise a tail moiety attached at either the 3' or 5'-end. The tail moiety is distinguished from the minor groove binding moiety, which is preferably also attached to the 3' or 5' end of the ODN, or to both. The tail moiety, if present, is attached to the end of the ODN which does not bear the minor groove binder moiety. By way of example, a tail moiety can be a phosphate, a phosphate ester, an alkyl group, an aminoalkyl group, a lipophilic group, or a molecule as disclosed, for example, in U.S. Pat. Nos. 5,512,667; 5,419,966; 5,574,142 and 5,646,126.

Variations of the bases, sugars, internucleoside backbone and tail moieties of the ODN portion of ODN-MGB-LF conjugates will be compatible with the ability of the conjugates to bind to a target sequence in a manner in which the minor groove binding moiety is incorporated in the newly formed duplex or triplex and thereby increases the melting temperature of the newly formed duplex, (i.e., increases the stability of the hybrid) as described in U.S. Pat. No. 5,801,155; International Patent Application No. PCT/IUS99/07487; Kutyavin et al., supra and Kamur et al. (1998) *Nucleic Acids Res.* 26:831–838; and with the ability of the LF to undergo hybridization-triggered fluorescence.

Formation of a hybrid between an ODN-MGB-LF conjugate and a target sequence results in an increase in fluorescence quantum yield or a change in the absorption and/or emission spectra of the LF. In light of the foregoing, those skilled in the art will readily understand that the primary structural limitation of the various component parts of the ODN portion of the ODN-MGB-LF conjugate are related to the ability of the ODN portion to form a hybrid with a specific target sequence. Thus, a large number of structural modifications, both known and to be developed, are possible within these bounds. Moreover, synthetic methods for preparing the various heterocyclic bases, sugars, nucleosides and nucleotides which form the ODN portion of ODN-MGB-LF conjugates are well-developed and known in the art. For example, $N_4,N_4$-ethano-5-methyldeoxycytidine, its nucleoside, nucleotide and/or oligonucleotides incorporating this base are synthesized in accordance with the teachings of Webb et al. (1986) *Nucleic Acids Res.*, 14:7661–7674; and Webb et al. (1986) *J. Am. Chem. Soc.* 108:2764. 4-aminopyrazolo[3,4-d]pyrimidine, 6-amino-4-hydroxypyrazolo[3,4-d]pyrimidine, their nucleosides, nucleotides and oligonucleotides incorporating these bases are synthesized in accordance with the teachings of Kazimierczuk et al. (1984) *J. Am. Chem. Soc.* 106:6379–6382. Preparation of oligonucleotides of specific predetermined sequence is conducted in accordance with the state of the art. A preferred method of oligonucleotide synthesis incorporates the teaching of U.S. Pat. No. 5,419,966.

Minor Groove Binders

In duplex DNA, the two antiparallel phosphodiester backbones do not lie directly opposite each other across the longitudinal axis of the duplex molecule; rather they are offset. As a result, the surface of the duplex contains two differently-sized grooves: a major groove and a minor groove. The minor groove lies between the 1' C atoms of the sugars on opposite strands, forming a cleft with a width of 5.7 Å, and a depth of 7.5 Å, which pursues a helical path along the surface of the duplex. Minor groove binders are molecules that, by virtue of their size and/or structure, are capable of interacting with this structural feature of duplex and triplex polynucleotides.

As noted supra, a minor groove binder (MGB) is a molecule that binds within the minor groove of double stranded nucleic acid, including DNA, RNA, DNA-RNA hybrids and nucleic acid chimeras, such as PNA/DNA chimeras. Minor groove binders have widely varying chemical structures, all of which are capable of binding within a minor groove having the geometry and dimensions described above. For example, certain MGBs are capable of forming a crescent-shaped three dimensional structure. Many minor groove binding compounds have a strong preference for A+T (adenine and thymine)-rich regions of the B form of double-stranded DNA. Without wishing to be bound by theory, it is possible that this preference is due, at least in part, to steric interference of MGB binding by the 2-amino group of guanine. However, if guanine is replaced by hypoxanthine in an ODN-MGB-LF conjugate, the potential for steric interference is reduced and binding of a MGB conjugate to a G+C-rich sequences is enhanced. Accordingly, ODN-MGB-LF conjugates incorporating a radical or moiety derived from a minor groove binder molecule having preference for both A+T-rich and G+C-rich regions are within the scope of the invention.

Examples of minor groove binding compounds which can, in accordance with the present invention, be covalently bound to ODNs to form the novel ODN-MGB-LF conjugates include certain naturally-occurring compounds such as netropsin, distamycin, lexitropsin, mithramycin, chromomycin $A_3$, olivomycin, anthramycin, and sibiromycin, as well as related antibiotics and synthetic derivatives. Certain bisquartemary ammonium heterocyclic compounds, diarylamidines such as pentamidine, stilbamidine and berenil, CC-1065 and related pyrroloindole and indole polypeptides, Hoechst 33258, 4'-6-diamidino-2-phenylindole (DAPI), and as a number of oligopeptides consisting of naturally-occurring or synthetic amino acids are minor groove binder compounds. The chemical structures of several exemplary MGBs are illustrated below.

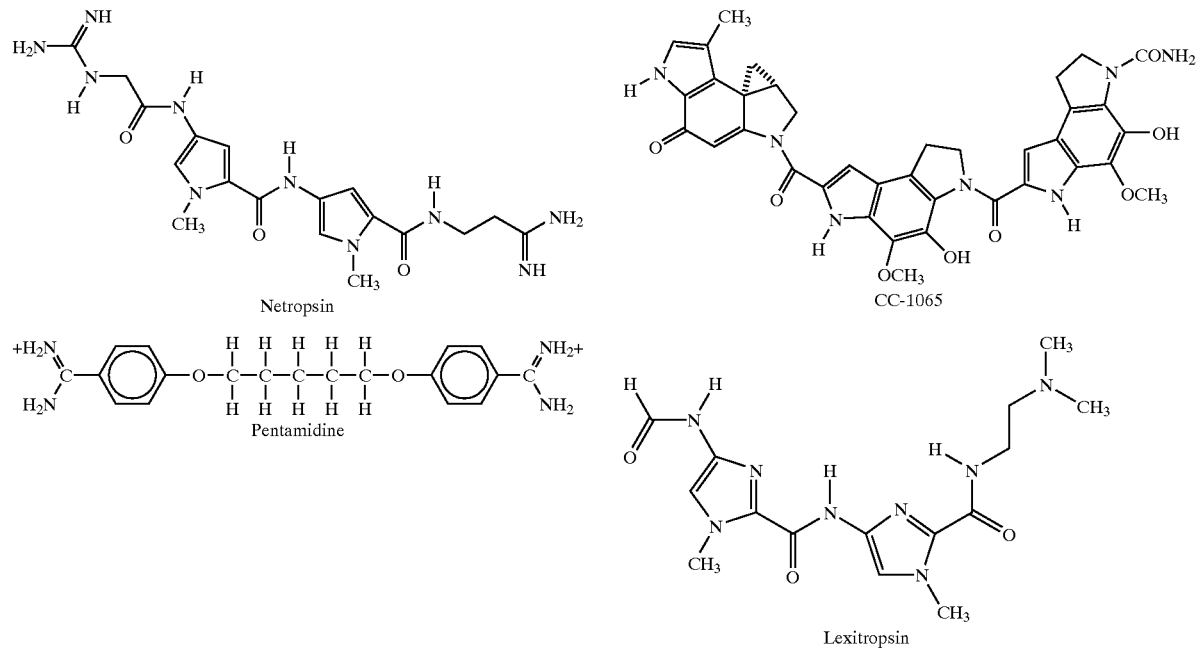

-continued
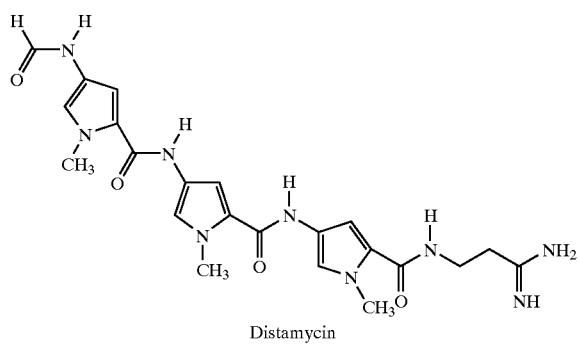
Distamycin
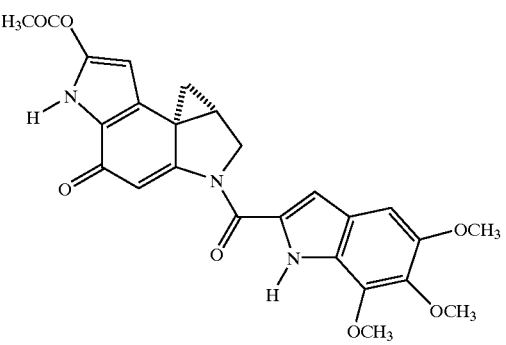
Duocarmycin SA
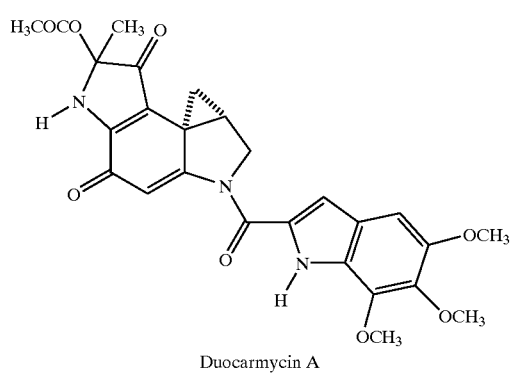
Duocarmycin A
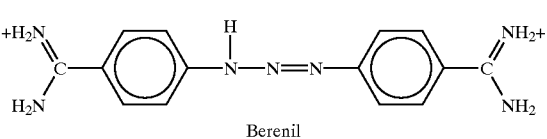
Berenil
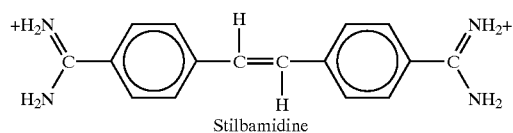
Stilbamidine
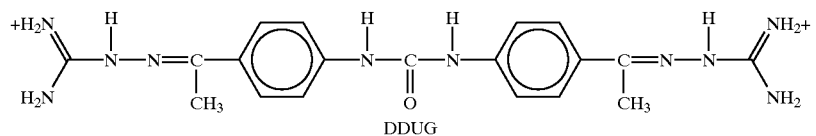
DDUG
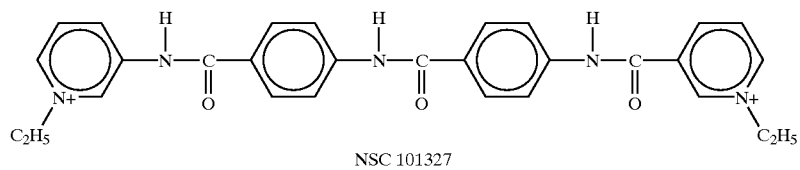
NSC 101327
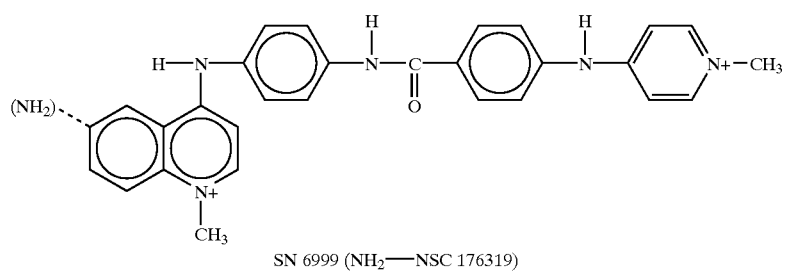
SN 6999 (NH₂—NSC 176319)
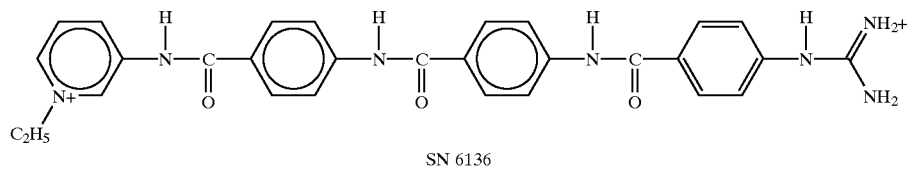
SN 6136

-continued

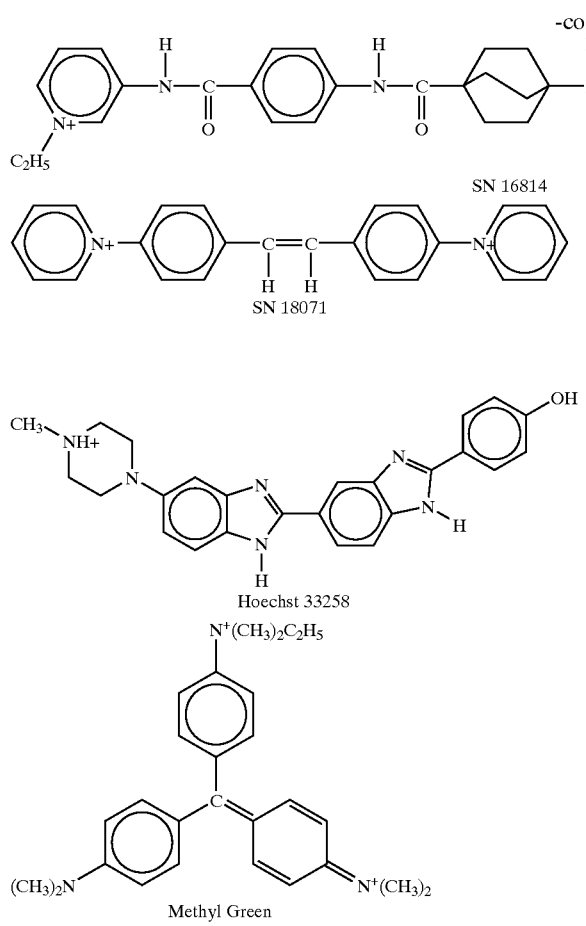

Hoechst 33258

Methyl Green

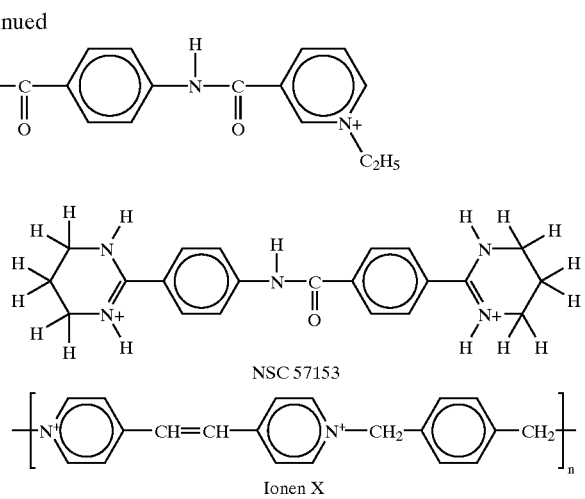

SN 16814

NSC 57153

Ionen X

For the purposes of the invention, a molecule is a MGB if it is capable of binding within the minor groove of double-stranded DNA, double-stranded RNA, DNA-RNA hybrids, DNA-PNA hybrids, hybrids in which one strand is a PNA/DNA chimera and/or polymers containing purine and/or pyrimidine bases and/or their analogues which are capable of base-pairing to form duplex, triplex or higher order structures comprising a minor groove, wherein said binding occurs with an association constant of $10^3$ $M^{-1}$ or greater. Such binding can be detected by any method known in the art including, but not limited to, well-established spectrophotometric methods, such as ultraviolet (UV) and nuclear magnetic resonance (NMR) spectroscopy, and gel electrophoresis. Shifts in UV spectra of nucleic acids are observed upon binding of a MGB molecule, as are changes in NMR spectra, analyzed utilizing the Nuclear Overhauser (NOSEY) effect. Gel electrophoresis detects binding of a MGB to double-stranded nucleic acid, because upon such binding the mobility of the double stranded nucleic acid changes.

As noted above, for the purposes of the invention, a molecule is a MGB if its association constant within the minor groove of a double stranded nucleic acid is $10^3$ $M^{-1}$ or greater. However, certain MGBs bind to high affinity sites with an association constant on the order of $10^7$ to $10^9$ $M^{-1}$.

Thus, both structural and functional guidelines for the identification of MGB moieties have been provided.

In addition to the molecular structure which causes minor groove binding, the MGB moiety can also comprise additional functions, as long as those functions do not interfere with minor groove binding ability.

In accordance with the present invention, the MGB molecule is derivatized, i. e., formed into a radical, and linked to appropriate chains of atoms that attach the MGB to the ODN and/or to the LF. The radical formed from the MGB molecule is hereinafter referred to as the "MGB moiety," and the covalent linker (which can be a chain having a backbone of up to approximately 100 atoms) that attaches the MGB moiety to the oligonucleotide or to the latent fluorophore is called the "linking group." Preferred MGB moieties are described in U.S. Pat. No. 5,801,155.

In a preferred embodiment, the minor groove binder moiety is covalently attached to either the 3'-or 5'-end of the oligonucleotide, through a terminal base, sugar or phosphate moiety, or through a tail moiety attached to one of these moieties. In additional embodiments, the MGB is attached to a nucleotide in an internal position, particularly to the base portion of the nucleotide.

Latent Fluorophores

The invention provides compositions and methods, involving the use of latent fluorophores, for detection of nucleic acids by hybridization-triggered fluorescence. A latent fluorophore is a molecule in which a physical property of the fluorophore is altered by its interaction with duplex or triplex nucleic acids, resulting in a change in the fluorescence spectrum and/or an increase in the fluorescence quantum yield at a particular wavelength, and/or a change in some other fluorescent property of the molecule. A change in fluorescence spectrum can include a change in the absorption spectrum and/or a change in the emission spectrum.

The majority of interactions between multi-stranded nucleic acids and their ligands can be described in terms of two types of binding interactions: intercalation and groove binding. Groove binding includes both major groove binding and minor groove binding. All of these binding interactions can be exploited in the design of latent fluorophores. For example, intercalation within a double-stranded DNA molecule can result in a decrease in the rotational freedom of a ligand, and/or a change in the dielectric environment that the ligand experiences. The invention provides examples of hybridization-triggered enhancement in quantum yield resulting from both intercalation and groove binding. Examples of latent fluorophores and methods for determining whether a molecule has the properties of a latent fluorophore are also provided.

Figure 1B:
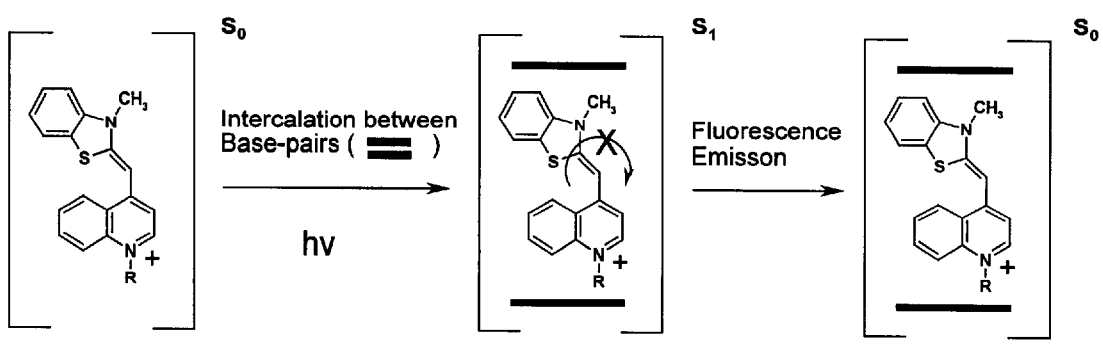
FIG. 1B shows fluorescent emission when rotation about the cyanine-methine bond is restricted, for example, by intercalation of the dye into a nucleic acid.

Certain cyanine dyes (see FIG. 1 for exemplary structure) are virtually non-fluorescent in the absence of nucleic acid. When free in solution these compounds transit from the excited singlet state ($S_1$) to the ground state ($S_0$) in a radiationless process involving loss of excitation energy by rotation about the cyanine methine bond (FIG. 1A). Cyanine dyes interact with double-stranded nucleic acid by intercalation. Intercalation prevents free rotation about the cyanine methine bond and causes the dye to lose excitation energy by fluorescence emission (FIG. 1B). Thus, without wishing to be bound by theory, a potential mechanism for hybridization-triggered fluorescence relates to restriction of rotation within a latent fluorophore following interaction with nucleic acid. Accordingly, molecules having these or similar properties are potential latent fluorophores.

In another aspect of the invention, hybridization-triggered increases in fluorescence quantum yield (or other changes in fluorescence properties) result from a change in the environment experienced by the latent fluorophore as a result of an interaction with double- or triple-stranded nucleic acid. For example, a fluorescent reporter group will experience a more hydrophobic environment (i.e., a decrease in dielectric constant) when intercalated or when positioned in the minor or major groove of a double-stranded nucleic acid. PRODAN (6-propionyl-2-dimethylaminonaphthalene) and 2-(dimethylamino)naphthalene-6-sulfonamide are examples of fluorogenic reporter groups having structural features such that their quantum yield and/or absorption maxima and/or emission maxima are sensitive to this type of change in environment. Compounds such as these have a large dipole moment in the excited state, as a consequence of charge delocalization between an electron-donating group and an electron-accepting group. Exemplary electron-donating groups include, but are not limited to, N or O atoms having an electron pair available for extended charge localization, for example, RO— and ($R_1$)($R_2$)N—, wherein R, $R_1$ and $R_2$ are independently H or alkyl, and wherein $R_1$ and $R_2$ can also be part of a 5- or 6-membered ring system. Exemplary electron-accepting groups include, but are not limited to, —$NO_2$, —C(=O)—, —C(=S)—, —C(=O)—NH—, —CN, —N(=O), —S(=O)$_2$—, —S(=O)$_2$—NH—, and —C=C(CN)$_2$. The group (—)N=C(—)(—) can also serve as an electron-accepting group, wherein N and C can both be part of a ring system or C alone can be part of a ring system. In general, electron-donating and -accepting groups and their properties are well-known to those of skill in the art.

Additional environment-sensitive fluorogenic species, capable of delocalizing electron density via conjugated electron donor-electron acceptor groups, include derivatives of 2-dimethylaminonaphthalene-6-sulfonamides and the isomeric species 5-dimethylaminonaphthalene-1-sulfonamides, 4-(N-methylamino)-7-nitro-2,1,3-benzoxadiazole, 6-anilinonaphthalene-2-sulfonamides, derivatives of pyridyloxazoles, 1-anilinonaphthalene-8-sulfonic acid, 2-anilinonaphthalene-6-sulfonic acid, 2-(p-toluidinyl)naphthalene-6-sulfonic acid, N-phenyl-1-naphthylamine, thiazole orange, oxazole yellow, thiazole blue, thiazole green, 4-(dicyanovinyl)julolidine, 4-dimethylamino-4'-nitrostilbene, Nile Blue and Nile Red. See, for example, Haugland, supra.

Compounds such as the aforementioned and their derivatives, whose fluorescence properties (such as quantum yield, absorption maximum and/or emission maximum) are sensitive to the polarity of their environment, can be coupled to a linking group for attachment to a MGB (see below) and used as latent fluorophores in the practice of the invention. As one example of the use of this type of latent fluorophore, Table 2, infra, shows an increase in fluorescence quantum yield for an oligonucleotide-MGB-(2-dimethylaminonaphthalene-6-sulfonamide) conjugate upon hybridization to a complementary DNA strand (conjugate #3, see also FIG. 5).

A number of commercially-available compounds, which exhibit environment-sensitive fluorescence after conjugation, containing various types of reactive groups, are also useful. These include 6-acryloyl-2-dimethylaminonaphthalene (acrylodan) and 4-fluoro-7-nitrobenzofurazan (NBD). In the synthesis of ODN-MGB-LF conjugates, their reactive group can be reacted with nucleophilic groups, for conjugation to a MGB moiety, by methods known to those of skill in the art. See, for example, Casas-Finet et al. (1992) *Proc. Natl. Acad. Sci. USA* 89:1050–1054.

Additional examples of latent fluorophores, which can be attached to ODN-MGBs using methods known in the art (e.g., Haugland, supra) include:

(1) derivatives of the structures represented by Formula 1

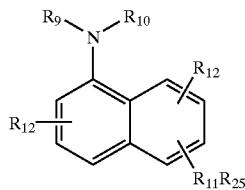

Formula 1 wherein $R_9$ and $R_{10}$ are independently —H or —(CH2)mCH3 where m=0 to 5, or $R_{25}$, or $R_9$ and $R_{10}$ together form a 5- or 6- membered ring system containing one or more C, N, O and/or S atoms;

$R_{11}$ contains one or more of the electron—withdrawing groups —C(=O)—, —C(=O)—O—, —C(=O)—NH—, —C(=S)—NH—, —N=N—, —S(=O)—, —S(=O)$_2$—, —S(=O)$_2$—NH—;

$R_{25}$ is —H or a linking group comprising a reactive group that reacts with hydroxyl, amino or sulfhydryl nucleophiles, and has a backbone between 1 and about 50 atoms long, wherein $R_{25}$ can contain the atoms H, C, N, O P and/or S, and wherein $R_{25}$ can contain one or more of the groups —S—, —NH—, —O—, —NH—C(=O)—, —NH—C(=O)—NH—, —NH—C(=S)—, —NH—C(=S)—NH—, —O—P(=O)$_2$—O —NH—, —O—P(=O)$_2$—O—; and each of $R_{12}$ is independently $R_{25}$, —H, a halogen; $NO_2$; —COOH; —CONH$_2$; —CONHR$_6$; —CON(R$_6$)$_2$; —OR$_6$; —SO$_3$H; —SO$_2$NH$_2$; —SO$_2$NHR$_6$; —SO$_2$N(R$_6$)$_2$; —SR$_6$; —R$_6$; C(=O)—O—R$_6$; or —N(R$_9$)(R$_{10}$);

wherein $R_6$ is —(CH$_2$)$_m$CH$_3$ where m=0 to 5;
wherein $R_9$ and $R_{10}$ are defined as above.

(2) derivatives of the structures represented by Formula 2

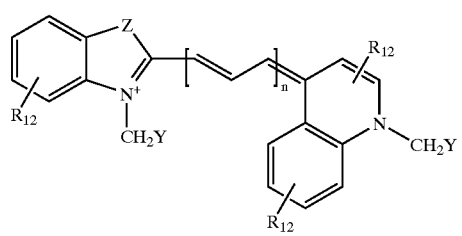

Formula 2 wherein Z is —O— or —S—;
n is between 0 and 5;
Y is H, —(CH$_2$)$_m$CH$_3$ where m=0 to 4, or $R_{25}$, wherein $R_{25}$ is defined as in Formula 1; and
$R_{12}$ is defined as in Formula 1.

(3) thiazole-indoline derivatives as shown in Formula 3

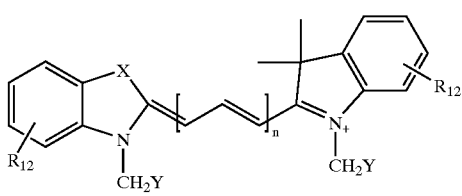

Formula 3 wherein X is —O— or —S—;
n is between 0 and 5;
Y is defined as in Formula 2; and
$R_{12}$ is defined as in Formula 1.

(4) derivatives of 4-(N-methylamino)-7-nitro-2,1,3-benzoxazole as represented by Formula 4

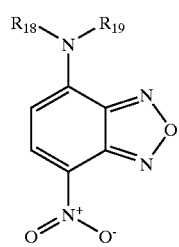

Formula 4 wherein $R_{18}$ and $R_{19}$ are independently $R_9$, $R_{10}$, $R_{11}$$R_{25}$ or $R_{25}$, where $R_9$, $R_{10}$, $R_{11}$, and $R_{25}$ are defined as in Formula 1.

(5) derivatives of the structures represented by Formula 5

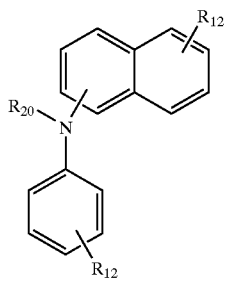

Formula 5 wherein $R_{12}$ is defined as in Formula 1; and
$R_{20}$ is —H, —(CH$_2$)$_m$CH$_3$ where m=0 to 5, or $R_{25}$, where $R_{25}$ is defined as in Formula 1.

(6) derivatives of the structures represented by Formula 6

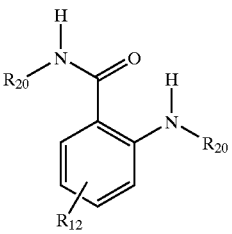

Formula 6 wherein $R_{12}$ is defined as in formula 1 and $R_{20}$ is defined as in Formula 5.

(7) derivatives of the structures represented by Formula 7

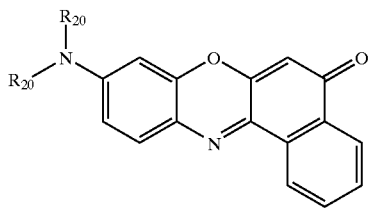

Formula 7 wherein $R_{20}$ is defined as in Formula 5.

(8) derivatives of the structures represented by Formula 8

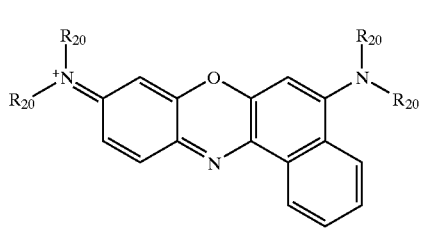

Formula 8 wherein $R_{20}$ is defined as in Formula 5.

(9) derivatives of the structures represented by Formula 9

Formula 9

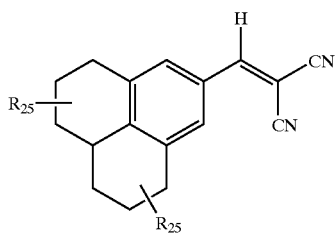

wherein $R_{25}$ is defined as in Formula 1.

(10) derivatives of the structures represented by Formula 10

Formula 10

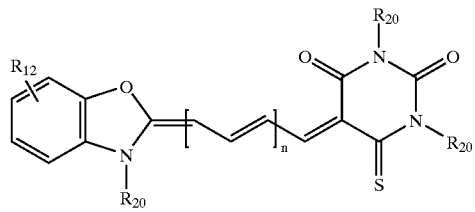

wherein $R_{12}$ is defined as in Formula 1 and $R_{20}$ is defined as in Formula 5.

(11) derivatives of the structures represented by Formula 11

Formula 11

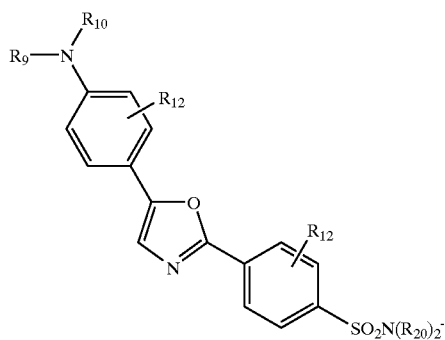

wherein $R_9$, $R_{10}$ and $R_{12}$ are defined as in Formula 1; and $R_{20}$ is defined as in Formula 5.

In one embodiment, a latent fluorophore is covalently linked to a MGB and/or an ODN via one or more linking groups. A linking group can be $R_{25}$, wherein $R_{25}$ comprises a backbone of from 1 to about 50 atoms, preferebly 40 atoms, more preferably 30 atoms, more preferably 20 atoms, still more preferably 10 atoms and most preferably 5–6 atoms containing C, H, N, O, S and/or P atoms, and comprises one or more of the groups —S—, —NH—, —O—, —NH—C(=O)—, —NH—C(=O)—NH—, —NH—C(=S)—, —NH—C(=S)—NH—, —O—P(=O)$_2$—O—NH— and —O—P(=O)$_2$—O—. See infra for further discussion of linking groups. In additional embodiments, linkage between a LF and a MGB and/or an ODN is via the groups $R_{11}R_{25}$, wherein $R_{11}$ includes an electron-withdrawing group such as, for example, —C(=O)—, —C(=O)—O—, —C(=O)—NH—, —C(=S)—NH—, —N=N—, —S(=O)—, —S(=O)$_2$— and —S(=O)$_2$—NH—, and $R_{25}$ is defined as described supra. When the configuration of the conjugate is ODN-MGB-LF, the LF is linked to the MGB by a single linking group; when the configuration of the conjugate is ODN-LF-MGB, two linking groups are attached to the LF: one to the ODN and one to the MGB.

The invention has identified structural features in organic molecules that qualify them as potential latent fluorophores. The general features of candidate compounds are shown below:

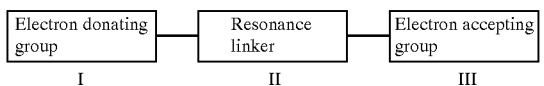

A candidate latent fluorophore thus requires three different structural features, designated I, II and III above. I and III are respectively electron donating and electron accepting groups connected to structural feature II, a resonance linker which, by allowing interaction between groups I and III, permits extended charge localization with large dipole moments. Electron-donating and electron-accepting groups are well known in the art. Exemplary electron-donating groups include N or O atoms with an electron pair available for extended localization, e.g. RO— or $(R_1)(R_2)N$—, wherein R, $R_1$ and $R_2$ are independently H or alkyl and wherein $R_1$ and $R_2$ can together form a 5- or 6-membered ring system. Exemplary electron-accepting groups include, but are not limited to —NO$_2$, —C(=O)—, —C(=S)—, —C(=O)—NH—, —CN, —N(=O), —S(=O)$_2$—, —S(=O)$_2$—NH—, —C=C(CN)$_2$ and (—)N=C(—)(—) wherein N and C can be part of a ring system. Resonance linker groups include aromatic ring systems and/or conjugated double and triple bond moieties. Structural features I and III are separated by at least one conjugated double or triple bond.

In another embodiment, methods for identification of environment-sensitive fluorophores are provided. A compound is tested by determining its fluorescent spectra in four solvents with different polarities. Solvents having the requisite properties will be apparent to those of skill in the art. In one embodiment, the solvents are water, methanol, ethanol and ethyl acetate; having dielectric constants of 78.54, 32.6, 24.3 and 6.02, respectively. As an example, the fluorescence intensities of a number of known LFs were evaluated in water and in ethanol as shown in Table 1. Based on these results, a compound whose fluorescent signal in ethyl acetate, ethanol or methanol is about six-fold or greater that its fluorescent signal in water is a candidate latent fluorophore. It is likely that even smaller differences in fluorescence between different solvents, i. e., on the order of two- or three-fold, is indicative of a candidate LF. Further evaluation of a candidate LF is accomplished by synthesis of its ODN-MGB conjugate and testing for hybridization-triggered fluorescence. In addition, a compound that exhibits changes in fluorescence excitation and/or emission maxima in less polar solvents, instead of or in addition to an increase in fluorescence quantum yield, is also a potential latent fluorophore.

TABLE 1
Fluorescence of known latent fluorophores in water and ethanol
| Compound | λ (nm) | Fluorescent Intensity (FL) | | $FL_{EtOH}/FL_{H2O}$ |
|---|---|---|---|---|
| | | Water | Ethanol | |
| 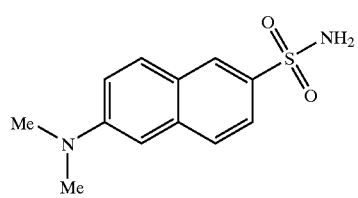 | 405 | 69 | 412 | 6 |
| 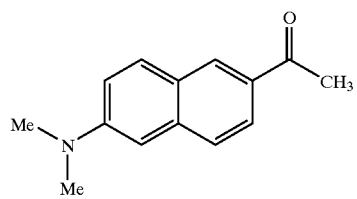 | 480 | 8 | 181 | 23 |
| 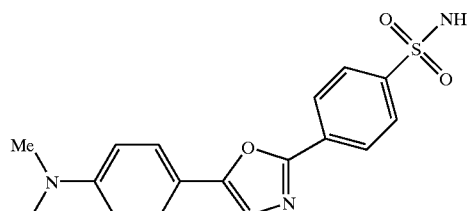 | 525 | 4 | 226 | 57 |
| 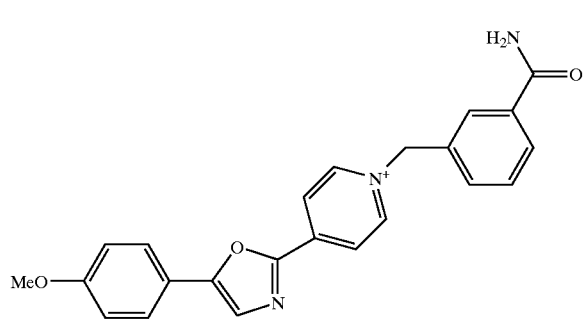 | 538 | 2 | 674 | 337 |
|  | 445 | 17 | 531 | 31 |

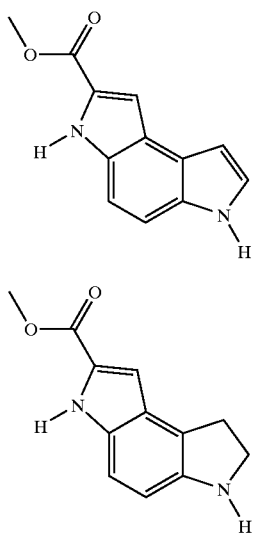

Environment sensitivity of fluorescence was tested for two related compounds, one of which (Compound A) contained structural features I, II and III as described above, and one of which (Compound B, a reduced derivative of Compound A) did not. These compounds were synthesized according to Boger et al. (1987) *J. Org. Chem.* 52:1521–1530. As predicted on the basis of its structural features, Compound A exhibited a 31-fold difference in fluorescence emission between its water and ethanol solutions. Reduced derivative B showed only a two-fold difference under similar conditions. In light of the results presented in Table 1, the environment-sensitive characteristics of Compound A suggest its use as a latent fluorophore.

Preferred embodiments of ODN-MGB-LF conjugates are those in which the latent fluorophore is covalently attached to the MGB and/or the ODN in a manner that maintains or enhances its ability to undergo hybridization-triggered fluorescence; for example, by allowing rotational freedom between the LF and the remainder of the conjugate. Methods for attachment of fluorophores to MGB and/or ODN moieties in this manner, and the chemical principles involved, are known in the art and are described infra and, for example, in Haugland, supra. Furthermore, the optimal structural relationship between a LF and the other components of the conjugate is one that results, upon hybridization, in projection of the LF into a non-polar region or into a region that restricts the rotational freedom of the LF, resulting in increased fluorescence.

Linking Groups

The ODN, MGB and LF moieties are covalently joined to one another by various linking groups. In one configuration, conjugates of the invention have the structure ODN-MGB-LF. For this configuration, preferably the linking groups are such that the linkage between the ODN and the MGB occurs through a chain of no more than about 100 atoms, preferably 80, more preferably 60, more preferably 40, more preferably 20, still more preferably 10, and most preferably about 5–6 atoms, and the linkage between the MGB and the LF occurs through a chain of no more than about 50 atoms, preferebly 40 atoms, more preferably 30 atoms, more preferably 20 atoms, still more preferably 10 atoms and most preferably about 5–6 atoms. Another configuration of the conjugates of the invention has the structure ODN-LF-MGB. In this configuration, the linkage between the ODN and the LF occurs through a chain of no more than about 50 atoms, preferebly 40 atoms, more preferably 30 atoms, more preferably 20 atoms, still more preferably 10 atoms and most preferably about 5–6 atoms and the linkage between the LF and the MGB occurs through a chain of no more than about 50 atoms preferebly 40 atoms, more preferably 30 atoms, more preferably 20 atoms, still more preferably 10 atoms and most preferably about 5–6 atoms.

Generally speaking, the linking group is derived from a bifunctional molecule such that one functionality (e.g., an amine) is attached, for example, to a 5' phosphate end of an ODN, and the other functionality (e.g., a carbonyl group) is coupled, for example, to an amino group of a minor groove binder moiety. Alternatively, a linking group can be derived from an amino alcohol so that the alcohol function is linked, for example, to a 3'-phosphate end of an ODN and the amino function is linked, for example, to a carbonyl group of a MGB moiety. Additional linking groups include amino alcohols (attached, for example, to the 3'-phosphate of an ODN via an ester linkage) linked to an aminocarboxylic acid which in turn is linked in a peptide bond to a carbonyl group of a MGB. See U.S. Pat. No. 5,801,155 for further disclosure related to linking groups. Thus, preferred embodiments of the linking group have backbones containing the atoms C, N, O, P and/or S and can contain one or more of the groups groups —NH—, —O—, —C(=O)—, —O—C(=O)—, —NH—C(=O)—, —C(=O)—NH—, —NH—C(=O)—NH—, —NH—C(=S)—, —NH—C(=S)—NH—, —N=N—, —O—P(=O)$_2$—NH—, —O—P(=O)$_2$—O—, —S(=O)—, —S(=O)$_2$—, —S(=O)$_2$—NH—, —S—, and —S—S—. Preferably the MGB moiety is separated by not more than approximately 100 atoms from the ODN and not more than approximately 50 atoms from the LF. Accordingly, more preferred embodiments of linking groups include, for example, —(CH$_2$)$_3$OC(=O)NH(CH$_2$)$_6$C(=O)— and —O(CH$_2$)$_6$NH—.

As mentioned supra, the presence of a latent fluorophore renders a composition readily detectable by an increase or decrease in a discernible physical or chemical characteristic upon hybridization to a target sequence. In one embodiment, a latent fluorophore is covalently attached to a minor groove binder moiety by a linking group. The 2-dimethylaminonaphthalene-6-sulfonyl function is an example of a preferred embodiment of a latent fluorophore, which can be attached to a carbonyl function of the minor groove binder through a —HN(CH$_2$)$_m$NH—bridge, where m is such that the length of the linker between the MGB and the LF is no more than about 50 atoms. The latent fluorophore can be coupled to one end of this bridge by chemistries known in the art, for example through the use of coupling groups such as —C(=O), —O—C(=O)—, —NH—C(=O)—, —NH—C(=S)—and —CH$_2$—.

Alternatively, a reactive group can be attached directly to a LF to facilitate its coupling to a linking group of a MGB or ODN. Such reactive groups include, but are not limited to, moieties such as carbonates, isocyanates, isothiocyanates, mono- or di-substituted pyridines, maleimides, aziridines, acid halides, sulfonyl halides, monochlorotriazines, dichlorotriazines, hydroxysulfosuccinimide esters, hydroxysuccinimide esters, azidonitrophenyls, azides, aldehydes, ketones, glyoxals and 3-(2-pyridyl dithio)-propionamide.

Hybridization-triggered Fluorescent Probes for Detection of Double-stranded Nucleic Acids ODN-MGB-LF conjugates can be used for detection of both single-stranded and double-stranded nucleic acid targets. For detection of double-stranded nucleic acids, the oligonucleotide component of the conjugate is a triplex-forming oligonucleotide (TFO), and binds in the major groove of the double stranded target via Hoogsteen, reverse Hoogsteen or equivalent base pairing, as is known in the art. The MGB component of the conjugate binds to the minor groove of the double-stranded target. Synthesis of conjugates capable of simultaneous binding of the TFO in the major groove and the MGB in the minor groove is accomplished by attaching the MGB to the TFO via a long flexible linker, having a length up to about 100 atoms, such that the flexible linker is able to wrap around one of the strands of the duplex target. TFO-MGB conjugates of this kind have been described. Lukhtanov et al. (1997a) *J. Am. Chem. Soc.* 119:6214–6225; and Lukhtanov et al. (1997b) *Nucleic Acids Res.* 25:5077–5084. In a TFO-MGB-LF conjugate designed for detection of a double-stranded target, the latent fluorophore will be anchored in the minor groove and will undergo either an increase in fluorescence intensity at a given wavelength or some other discernable change in fluorescent properties as described supra.

The MGB-LF portion of the conjugates can also gain access to the minor groove of target double-stranded DNA by threading through the base-pair stack, from the major to the minor groove. The threading phenomenon has been previously described in the literature, mostly associated with threading intercalators which are intercalating moieties bearing bulky side chains that can pass through the base pair stacks of duplex nucleic acids. The Pluromycins, which are known to thread the DNA structure, placing carbohydrate residues into both grooves, provide an example. Hansen et al. (1996) *Acc. Chem. Res.* 29:249–258.

Synthesis of MGB-ODN-LF Conjugates

Preferred embodiments of minor groove binder moieties are oligopeptides derived from 1,2-dihydro-3H-pyrrolo[3,2-e]indole-7-carboxylic acid (CDPI) and from N-methylpyrrole-4-carbox-2-amide (MPC). These have been described in detail in U.S. Pat. No. 5,801,155, wherein a process was disclosed for preparing the tripeptide CDPI$_3$, which thereafter can be coupled, in accordance with the present invention, and with or without minor modification, to an ODN to form a portion of a preferred ODN-MGB-LF conjugate.

In Reaction Scheme 1, a general method for coupling a 3'-amino-tailed or 5'-amino-tailed ODN with a tetrafluorophenyl (TFP) ester of an exemplary minor groove binding oligopeptide is illustrated. The scheme shows the use of a TFP-activated exemplary minor groove binding compound obtained in accordance with U.S. Pat. No. 5,801,155; however, this general method is suitable for the coupling of any TFP-activated minor groove binding compound to an ODN. Reference numerals 1a and 1b in Reaction Scheme 1 refer to exemplary compounds obtained in accordance with methods described in U.S. Pat. No. 5,801,155, the disclosure of which is expressly incorporated herein by reference.

A 5'- or 3'-amino-tailed ODN can be synthesized by conventional methods; for example an aminohexyl residue can be attached to either end of an ODN by using commercially available MMT-aminohexyl phosphoramidite (5' tail) or N-Fmoc-aminohexyl-CPG (3' tail). Alternatively, an amino-tailed ODN can be synthesized in accordance with the methods described in U.S. Pat. No. 5,419,966, the disclosure of which is expressly incorporated herein by reference. In accordance with the present scheme, the amino-tailed ODN is converted into a cetyltrimethylammonium salt to render it soluble in organic solvents, and the tetrafluorophenyl ester-activated MGB molecule is condensed therewith, preferably using DMSO as a solvent.

Reaction Scheme 2 discloses another method for coupling an active ester of a minor groove binder molecule to a 5'- or 3'-amino tailed ODN (2).

Reaction Scheme 1

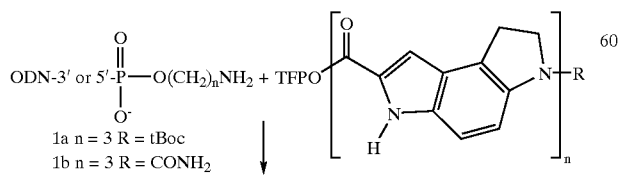

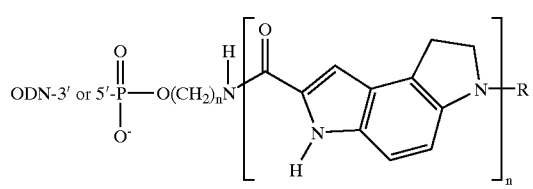

Reaction Scheme 2

CPG bearing 5'-amino tailed ODN

1. TFP CDPI$_3$ (1b Scheme 1)
2. Conc. NH$_3$

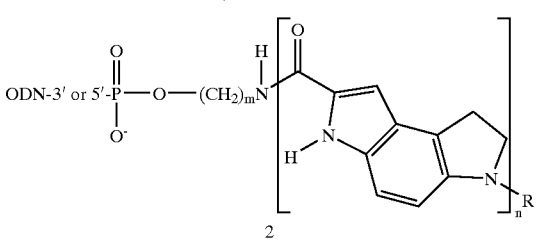

The TFP ester of the tripeptide (n=3) derived from carbamoyl-1,2-dihydro-3H-pyrrolo[3,2-e]indole-7-carboxylic acid (TFP-CDPI$_3$) is shown as an exemplary MGB; however, it will be clear to one of skill in the art that the generic principles disclosed in connection with this reaction scheme can be used with other minor groove binder molecules as well. In this method, the ODN comprises a tail moiety (wherein m=1 to 99) comprising a free terminal amino group, and remains attached to a CPG support during the addition of the MGB. Such an ODN is obtained, for example, by stepwise synthesis on a CPG support, using a MMT-aminohexyl phosphoramidite in the terminal addition step. This generates a CPG-bound ODN having a 5' tail comprising an amino group protected with a monomethoxytrityl (MMT) group. After synthesis of the ODN is complete, the MMT group is removed from the amino group using conditions under which the ODN remains attached to the CPG support, for example, by treatment with 3% trichloroacetic acid in $CH_2Cl_2$. In accordance with Reaction Scheme 2, the free amino group of this CPG-bound, amino-tailed-ODN is condensed with an active ester (e.g., TFP-CDPI$_3$, 1b) or with a similarly activated form of a minor groove binder. The ODN-MGB conjugate is thereafter removed from the CPG support by conventional methods, preferably by treatment with ammonia. Alternatively, a CPG-bound, 3'-amino-tailed ODN is obtained in accordance with the disclosure of U.S. Pat. No. 5,419,966, and references cited therein.

Another exemplary protecting group is the 9-fluorenylmethoxycarbonyl (Fmoc) group, which is removed by base treatment, as is known to those of skill in the art. Additional protecting groups, such as carbamate protecting groups, amide protecting groups and a series of special protecting groups are described in Green, T. W. & Wuts, P.G. M. in *Protective Groups in Organic Synthesis*, $2^{nd}$ Edition, John Wiley and Sons, Inc, N.Y., pp. 441–452. 1991.

Synthesis of 1-(3-hydroxypropyl)-thiazole orange (Compound 4 wherein q=3) was carried out in two steps, using methodology similar to that used for the synthesis of 1-(3-iodopropyl)-thiazole orange (Reaction Scheme 3). Benson et al. (1993) *Nucleic Acids Res* 21:5727–5735; Brooker et al. (1941) *J. Am. Chem. Soc.* 63:3192–3202; and Brooker et al. (1942) *J. Am. Chem. Soc.* 64:199–210. Conversion to the activated 4-nitrophenyl carbonate derivative (5) was accomplished by the reaction of 4 with 4-nitrophenyl chloroformate. Alternatively, a reactive group can be introduced at the 3-position of 2-(methylthio)-1,3-benzothiazole using reactions described by Brooker et al. (1941, 1942), supra. In addition, substituents such as —H, —halogen, —NO$_2$, —SO$_3$H, —COOH, —CONHR$_6$, —CON(R$_6$)$_2$, —OR$_6$, —SO$_2$NHR$_6$, —SO$_2$N(R$_6$)$_2$ and —SR$_6$; wherein R$_6$=—(CH$_2$)$_m$CH$_3$ and m=0 to 5; can be introduced on either ring of compound 3 as well as the on the phenyl ring of 2-(methylthio)-1,3-benzothiazole.

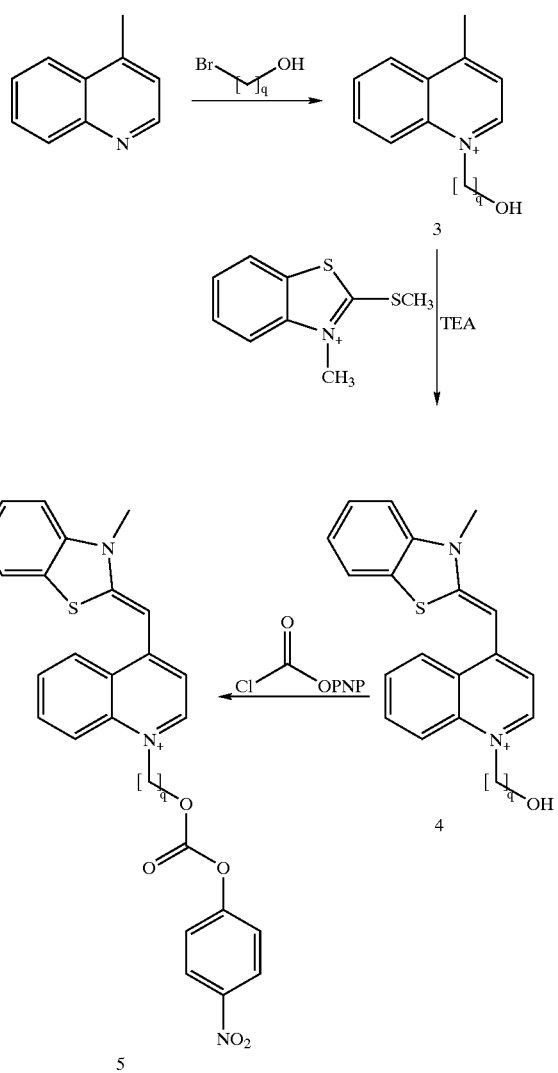

Reaction Scheme 3

Another preferred method for preparing a ODN-MGB-LF conjugate is shown in Reaction Schemes 4 and 5. Reaction Scheme 4 shows the synthesis of a MGB with reactive groups at both ends (12) for use in Reaction Scheme 5. The amino group of 6-aminohexanoic acid (n=5) was blocked with a MMTr group to form intermediate 6, whose carboxylic acid group was then activated with tetrafluorophenyltrifluoroacetate to yield intermediate 7. Reaction of 7 with methyl pyrrolo[4,4-e]indoline-7-carboxylate yielded the methyl ester 8 which was converted to the acid 9. Reaction of 9 with 3-(pyrrolo[4,5-e]indolin-7-ylcarbonyl)pyrrolo[4,5-e]indoline-7-carboxylate, followed by consecutive LiOH and TFP-TFA treatment yielded the CDPI$_3$ conjugate (12) containing a terminal MMTr-protected amino group and a TFP-protected ester at the other terminus. Conjugation of novel reagent 12 at one of its ends to an ODN and the other of its ends to a LF is possible by virtue of its terminal reactive groups.

Reaction Scheme 4
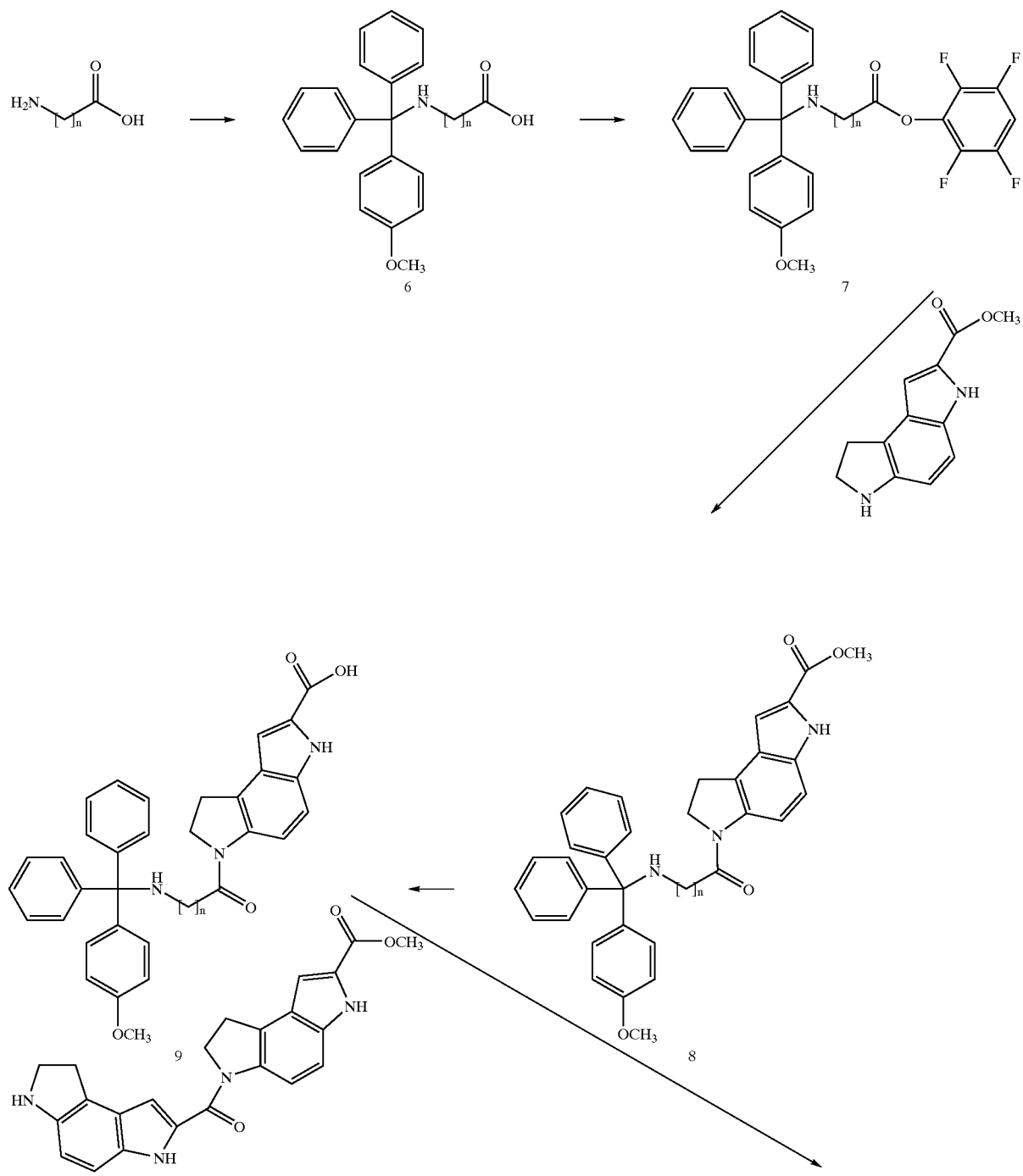

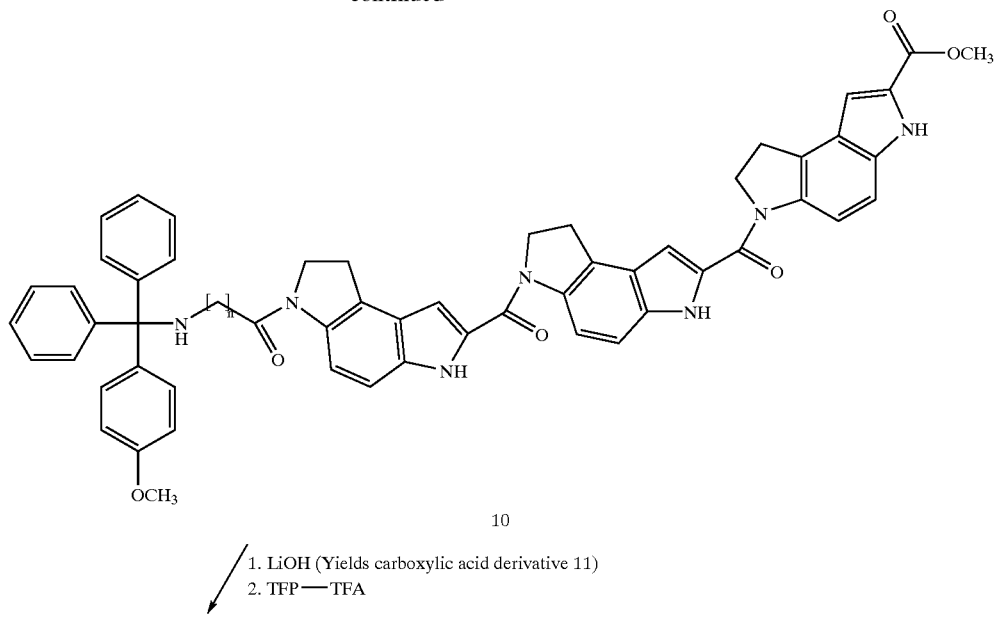

10

1. LiOH (Yields carboxylic acid derivative 11)
2. TFP — TFA

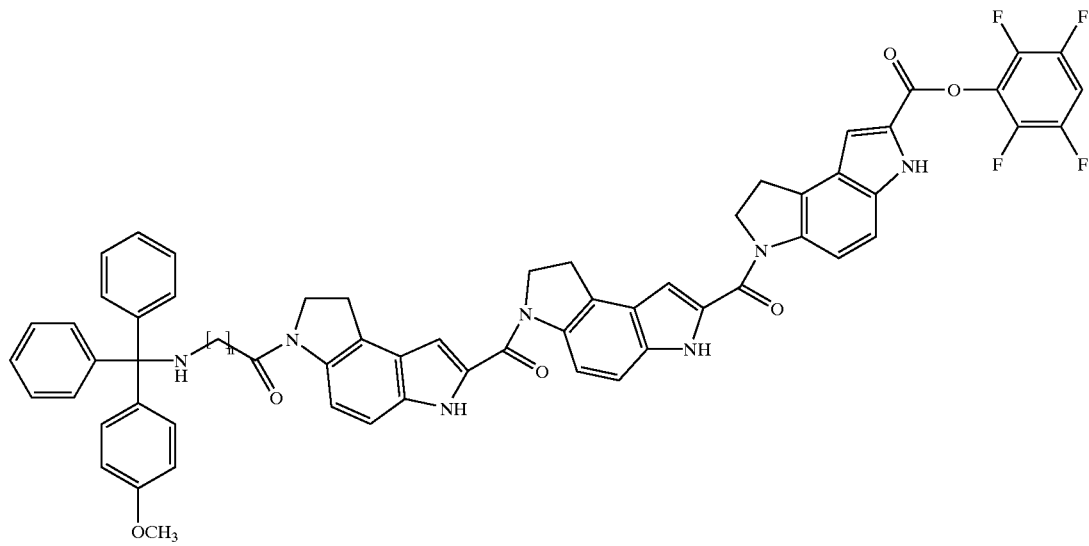

12 n = 1–48

For example, in Reaction Scheme 5, conjugate 12 is reacted with an ODN containing a 5'-aminoalkyl group to yield intermediate 13. Removal of the MMTr group with 80% acetic acid, and subsequent reaction with the activated carbonate (5) from Reaction Scheme 3, yielded the ODN-CDPI$_3$-TO (thiazole orange) conjugate 14. It is clear that similar reactions can be used to introduce different linkers between the MGB and the ODN and LF, respectively, to generate conjugates with the general formula indicated by Formula 12, where each of n and q is at least one, the sum of n and q is no greater than 46, and m=1–99.

Formula 12

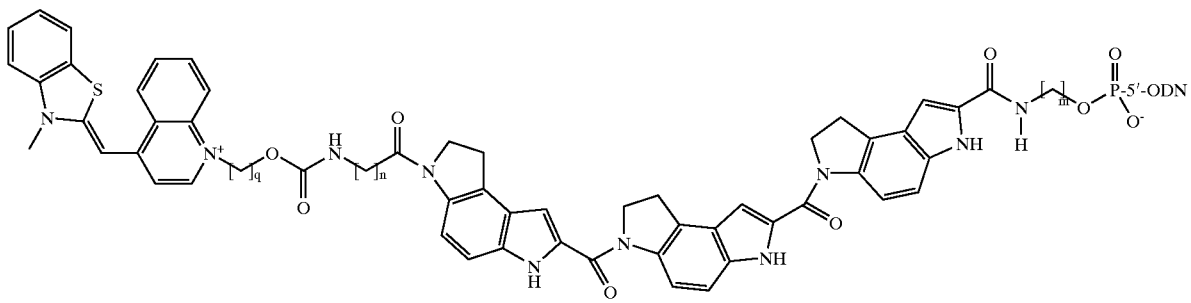

Furthermore, it is clear to those of skill in the art that a number of different MGBs and LFs, as disclosed herein, can be used in the reactions described above, to generate a wide variety of ODN-MGB-LF conjugates of this particular configuration.

U.S. Pat. No. 5,801,155, as shown in Reaction Scheme 7. After deprotection with TCA/CH$_2$Cl$_2$, the CPG derivative was used for standard oligonucleotide synthesis to obtain the required oligonucleotide sequence. Cleavage of the ODN from the CPG with ammonia yielded intermediate 16, which

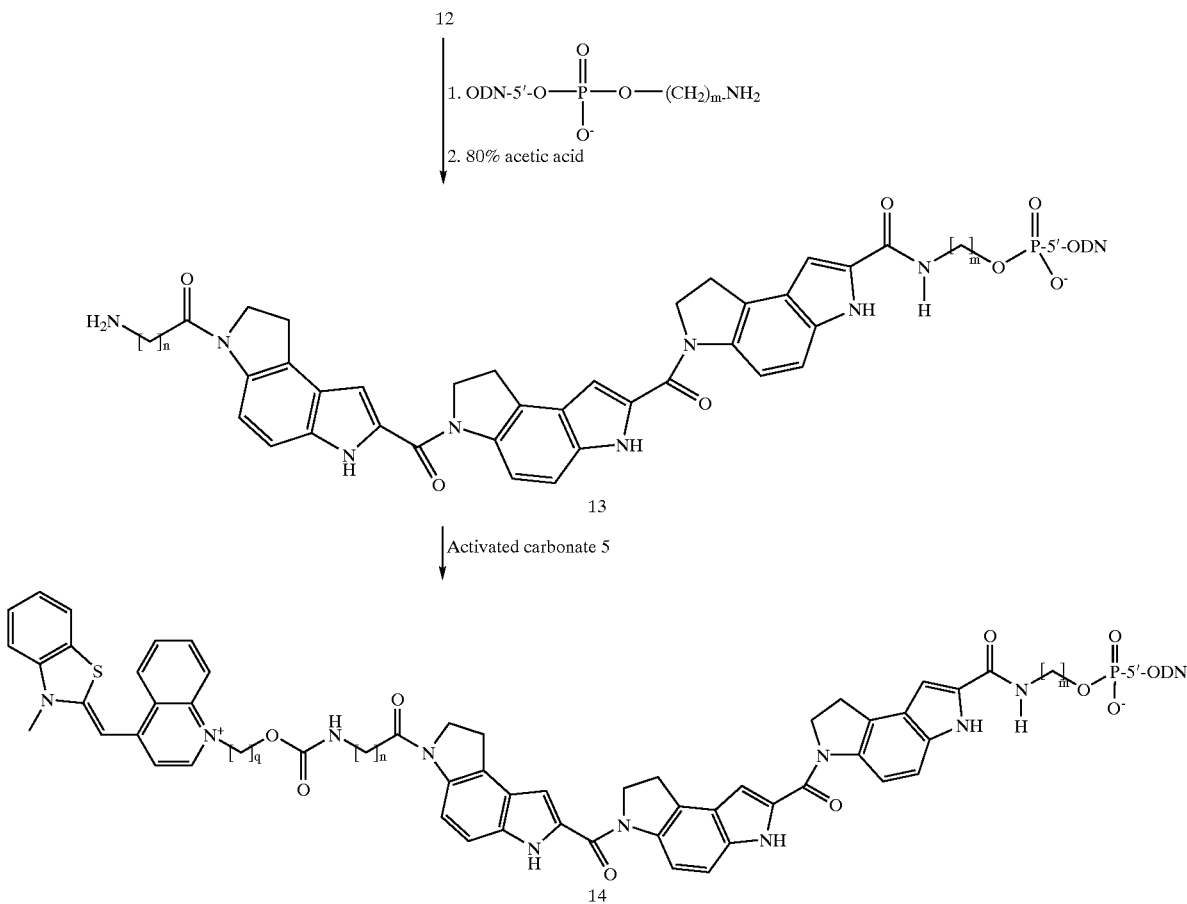

$m = 1–99$
$n \geq 1$
$q \geq 1$
$n + q \leq 46$

Reaction scheme 6 discloses another preferred method for preparing a 3'-ODN-MGB-LF conjugate. Intermediate 15 is synthesized by a modification of the methods disclosed in was coupled to an amine-reactive latent fluorophore to give the desired ODN-MGB-LF conjugate 17.

Reaction Scheme 6
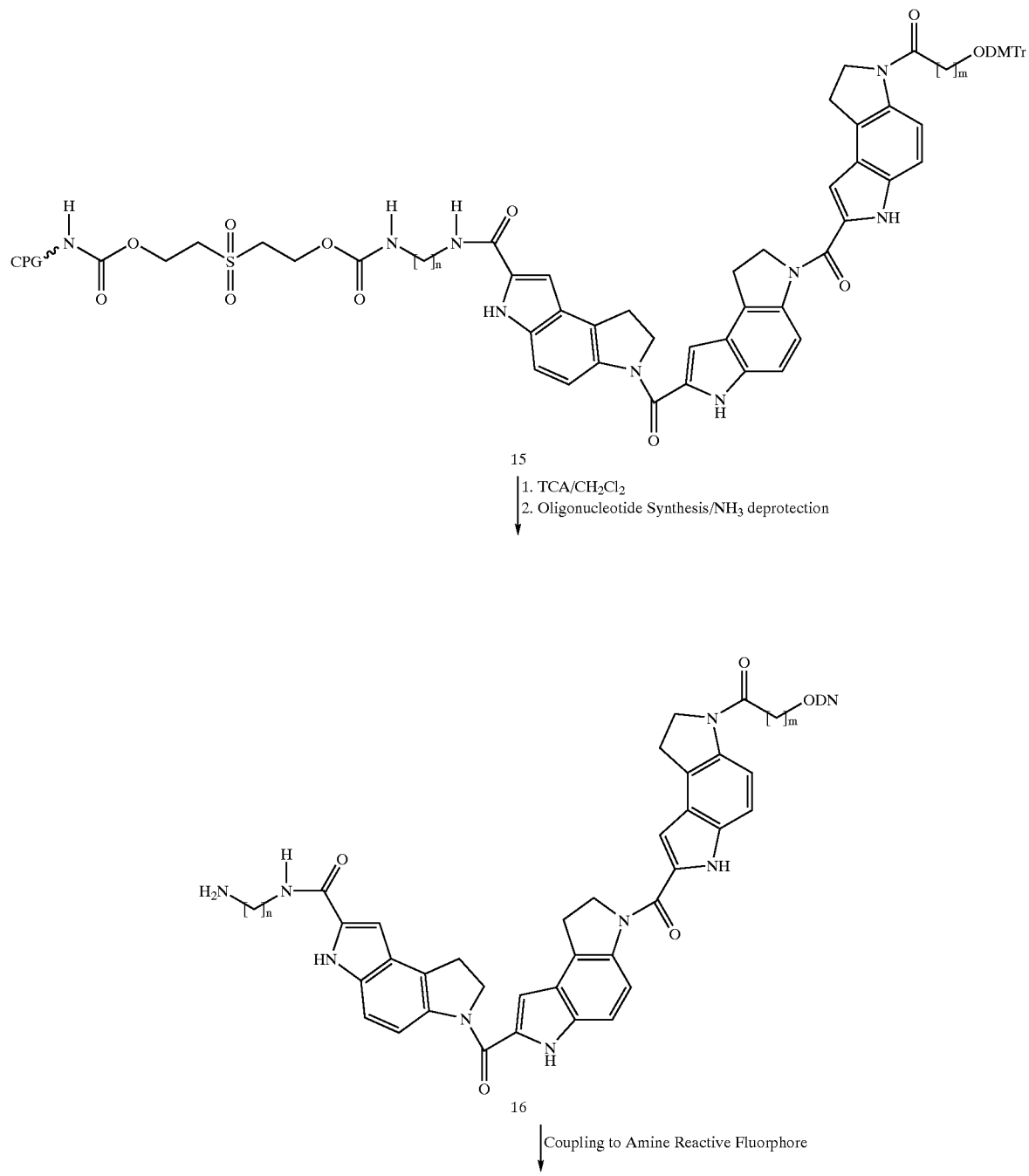

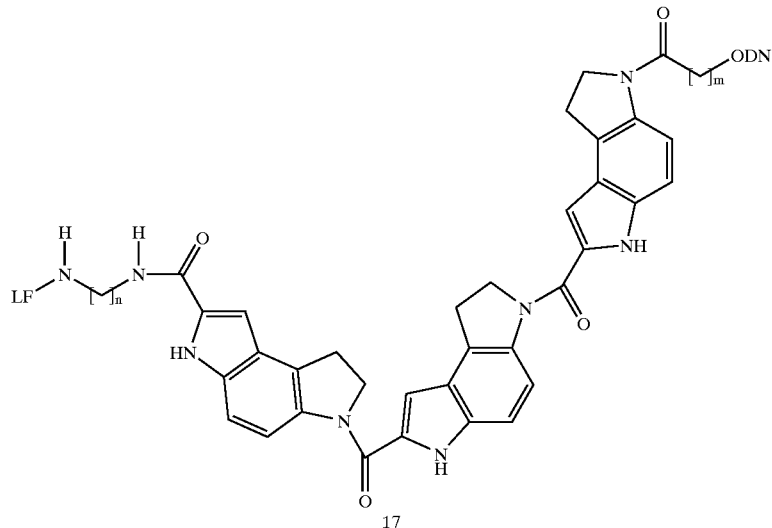

17 m = 1–100
n = 1–47

Intermediate 15 was prepared as shown in Reaction Scheme 7, starting with the reaction of p-nitrophenyl chloroformate with 2,2'-sulfonyldiethanol to yield 18. This compound was successively reacted with (3-aminopropyl)[(4-methoxyphenyl)diphenylmethyl]amine and activated with p-nitrophenyl chloroformate to yield 20. After the reaction of 20 with long chain amino CPG, deprotection with TCA/$CH_2Cl_2$ and reaction with activated ester 24, intermediate 22 was obtained. TFA deprotection of 22 followed by reaction with 25 gave intermediate 23 which was deprotected with TFA and reacted with p-nitrophenyl-4-O—DMT butyrate to provide the desired intermediate 15.

Reaction Scheme 7

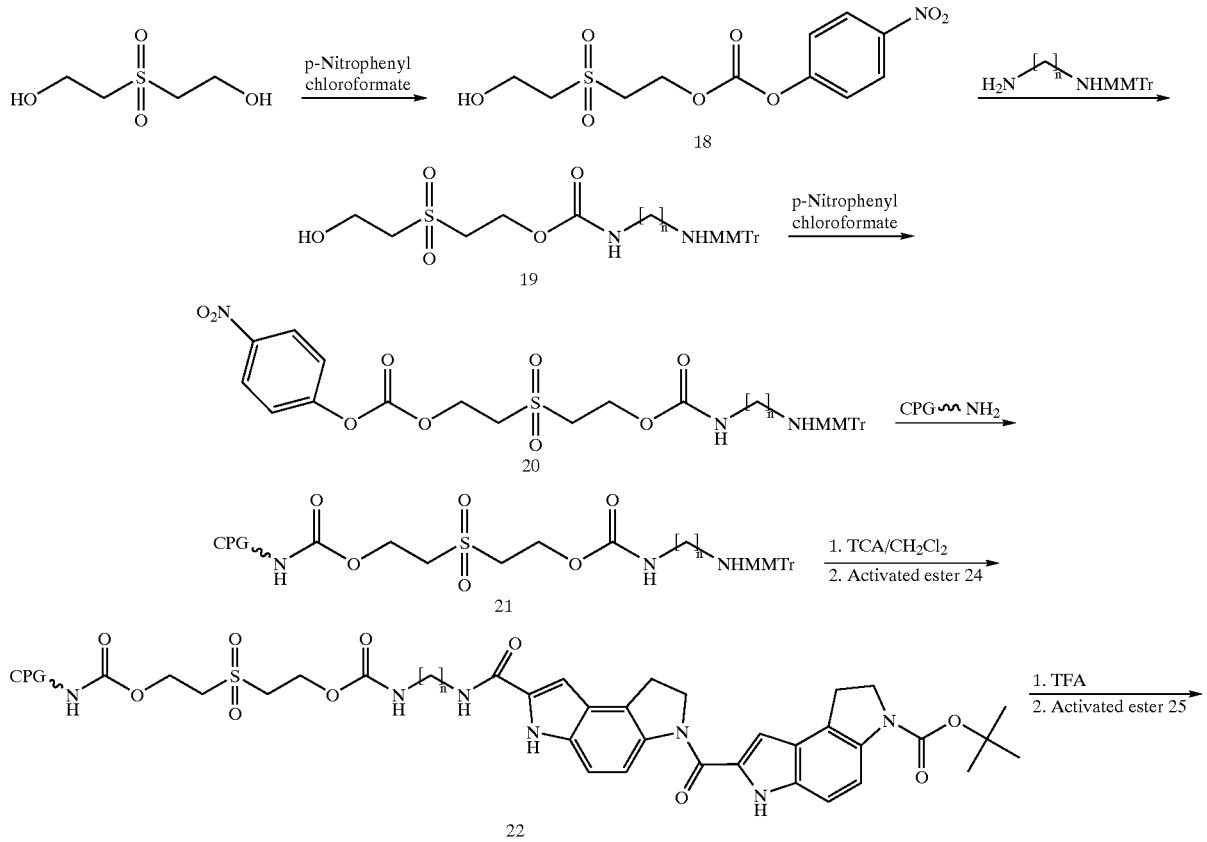

-continued
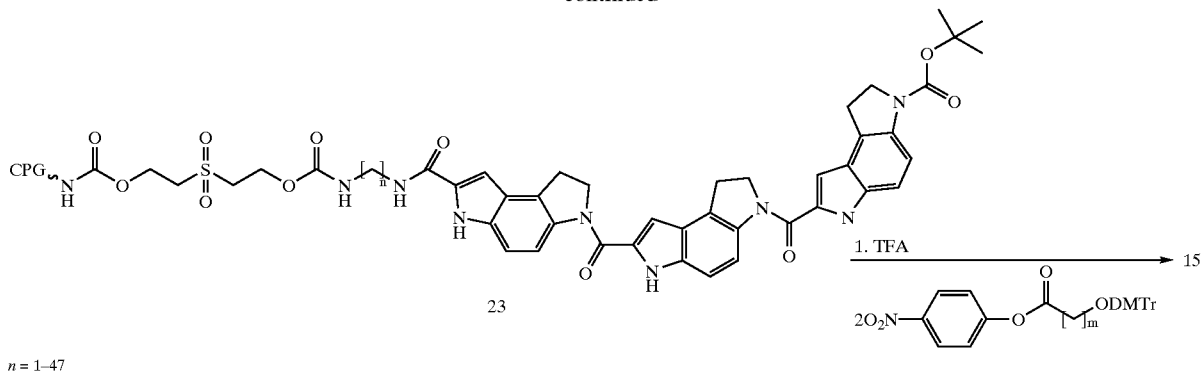
23
n = 1–47
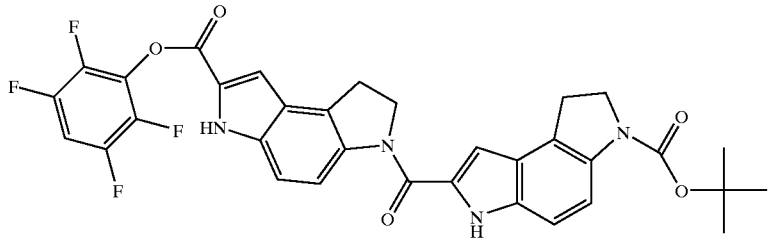
24
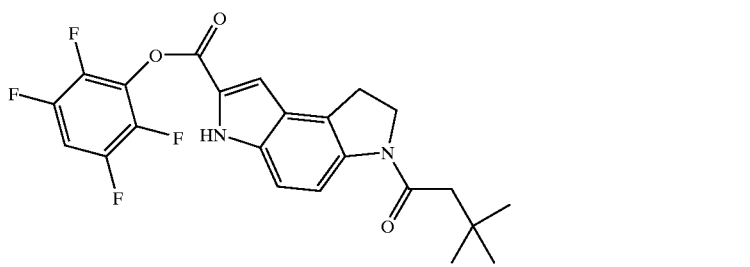
25
More generally, intermediates equivalent to compound 15 can be used for synthesis of ODN-MGB-LF conjugates. These intermediates contain a cleavable linker K between the CPG moiety and the MGB moiety, as shown in Formula 13 below:
Formula 13
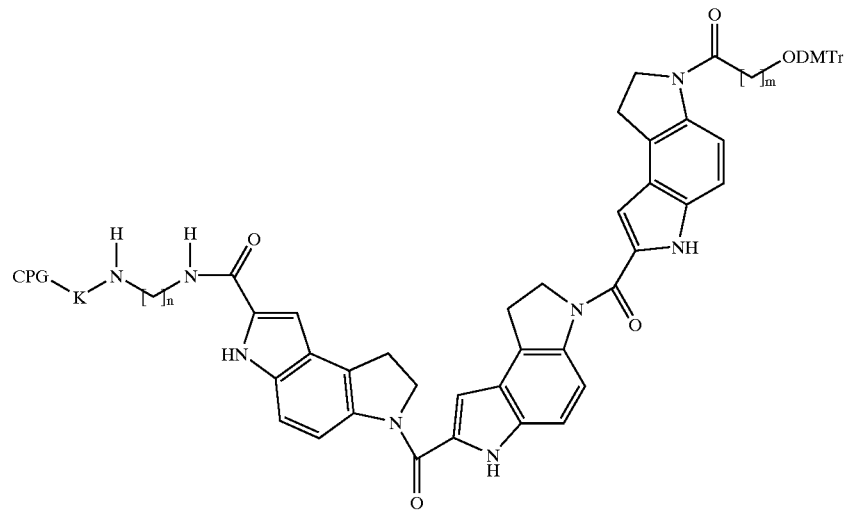
m = 1–99
n = 1–47

A variety of cleavable linkers useful for interposition between a CPG and a MGB, as shown in formula 13 by K, are known in the art. These include, but are not limited to, phosphodiester groups modified with a linker bearing an amino, thiol or hydroxyl group, and hydroquinone-O,O'-diacetic acid linkers. Lyttle et al. (1997) *Bioconjug. Chem.* 8:193–198; and Pon etal. (1997) *tetrahedron* 39:3327–3330. CPG supports with attached cleavable linkers are also available and include, for example, universal solid suppports and long-chain alkylamidopropanoic acid CPG. Scott et al. (1994) "Innovations and Perspectives in solid Phase Synthesis" 3$^{rd}$ International Symposium, ed. R.Epton, Mayflower Worldwide, pp. 115–124; and Damha et al. (1990) *Nucleic Acids Res.* 18:3813–3812.

In another embodiment, the LF can be incorporated on the linker between the ODN and MGB, rather than as shown in compound 17, Reaction Scheme 5, where the ODN and LF are on opposite ends of the MGB. To achieve this, Reaction Scheme 5 is modified, such that the ODN contains an appropriately-blocked hydroxyalkyl amine group at its 5' end. The amino group, after deprotection, is used to attach the MGB; and the hydroxyl group, after deprotection and activation, is used to attach the LF. For example, the CPG-(CDPI)$_3$-DMTr intermediate described by Lukhtanov et al. (1996) *Bioconj. Chem.* 7:564–567 is reacted with the phosphoramidite of 2-(4-Fmoc-aminobutyl)-1-(DMTrO)-propane-3-ol (Clontech, Palo Alto, Calif.), followed by standard oligonucleotide synthesis. After synthesis of the desired oligonucleotide is complete, cleavage from the CPG, followed by removal of the Fmoc blocking group, allows attachment of a LF to the amino group of the linker using reagent 5.

In another embodiment, the LF is attached at a site internal to the MGB, as follows. Reaction scheme 4 can be modified such that 7-(methoxycarbonyl)-4-[(phenylmethoxy)carbonylamino]pyrrolo[3,2-e]indoline-2-carboxylic acid (Boger et al. (1992) *J Org. Chem.* 57:1277–1284) is reacted with methyl 3-(pyrrolo[4,5-e]indolin-7-ylcarbonyl)pyrrolo[4,5-e]indoline-7-carboxylate (Boger et al., supra) in the presence of a coupling reagent to form the equivalent of 10, which after H$_2$/Pd/C treatment yields methyl 2-[2-{[3-[{5-amino-3-[(tert-butyl)oxycarbonyl]pyrrolo[4,5-e]indolin-7-yl}carbonyl]pyrrolo[4,5-e]indolin-7-yl]carbonyl}-3-pyrrolino[3,4-e]indolin-8-yl]acetate. This compound contains a free primary amino group which can be used for attachment of the LF, a t-Boc-protected nitrogen and a methyl ester-protected carboxylic acid. Either of the protected groups can be used for attachment of the oligonucleotide.

Characteristics of Hybridization-triggered Fluorescence with ODN-MGB-LF Conjugates Free cyanine dyes, such as TO, bind to double- and triple-stranded nucleic acid in a non-sequence-specific fashion or, at best, with only broad sequence preferences. By contrast, cyanine dyes and other latent fluorophores, when present in an ODN-MGB-LF conjugate, interact with nucleic acid based upon hybridization of the ODN portion of the conjugate with its complementary target. Thus, unlike free (unconjugated) dyes, ODN-MGB-LF conjugates bind with high specificity to sequences complementary to their ODN portion, and are capable of discriminating between closely-related DNA sequences with similar hybrid melting temperatures.

For example, an exemplary latent fluorophore is the cyanine dye thiazole orange (TO), which becomes highly fluorescent upon intercalation into double-stranded DNA. However, free TO binds in a sequence-independent fashion to double-stranded DNA, and thus cannot be used as a sequence-specific diagnostic probe. However, as part of an ODN-MGB-LF conjugate, the fluorescent potential of TO is coupled with the sequence specificity imparted by the oligonucleotide, to obtain sequence-specific fluorescent detection of a complementary target sequence.

Figure 2A:
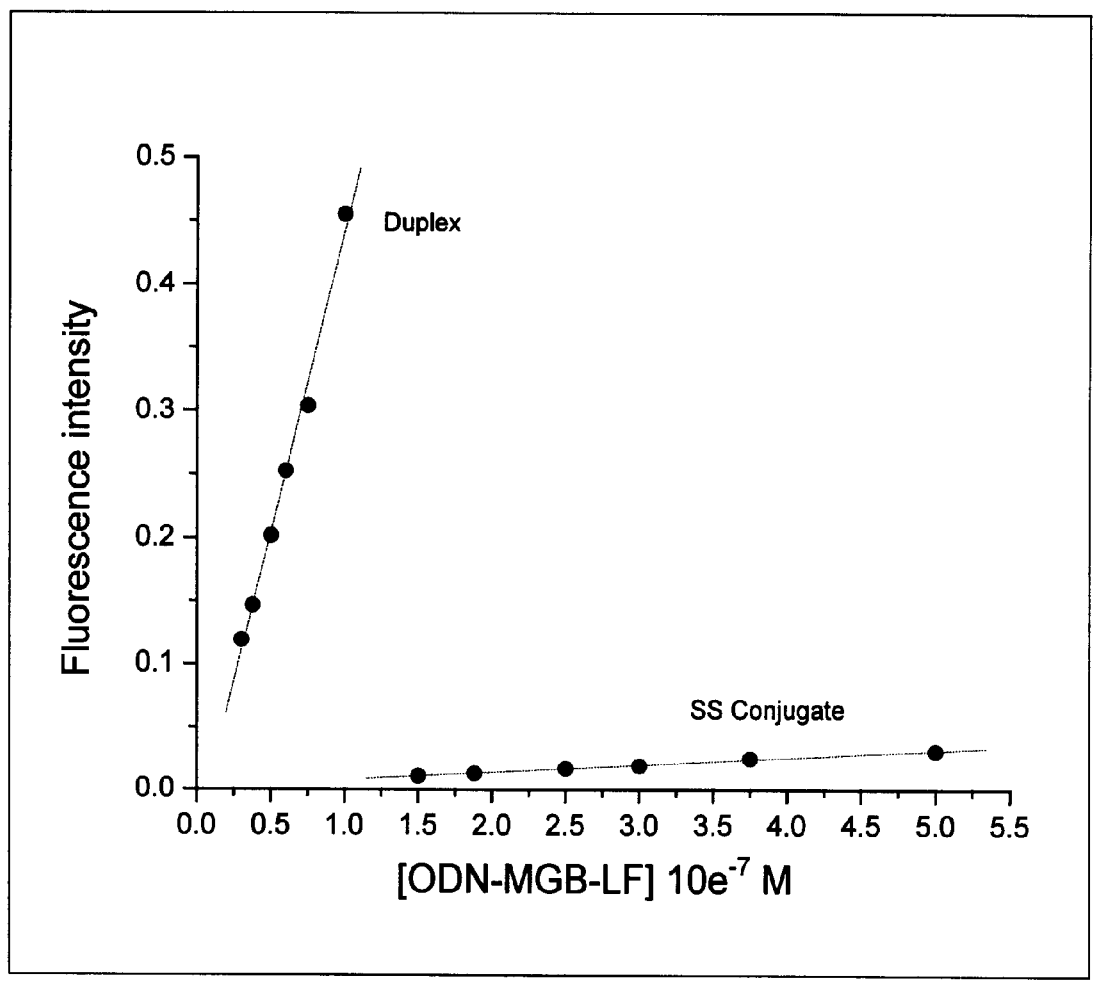
FIG. 2A shows hybridization-triggered, fluorescence with a conjugate, TO-MGB-5'-CAATTTAAAGAA-3' (SEQ ID NO: 1), containing an AT-rich sequence.
Figure 2B:
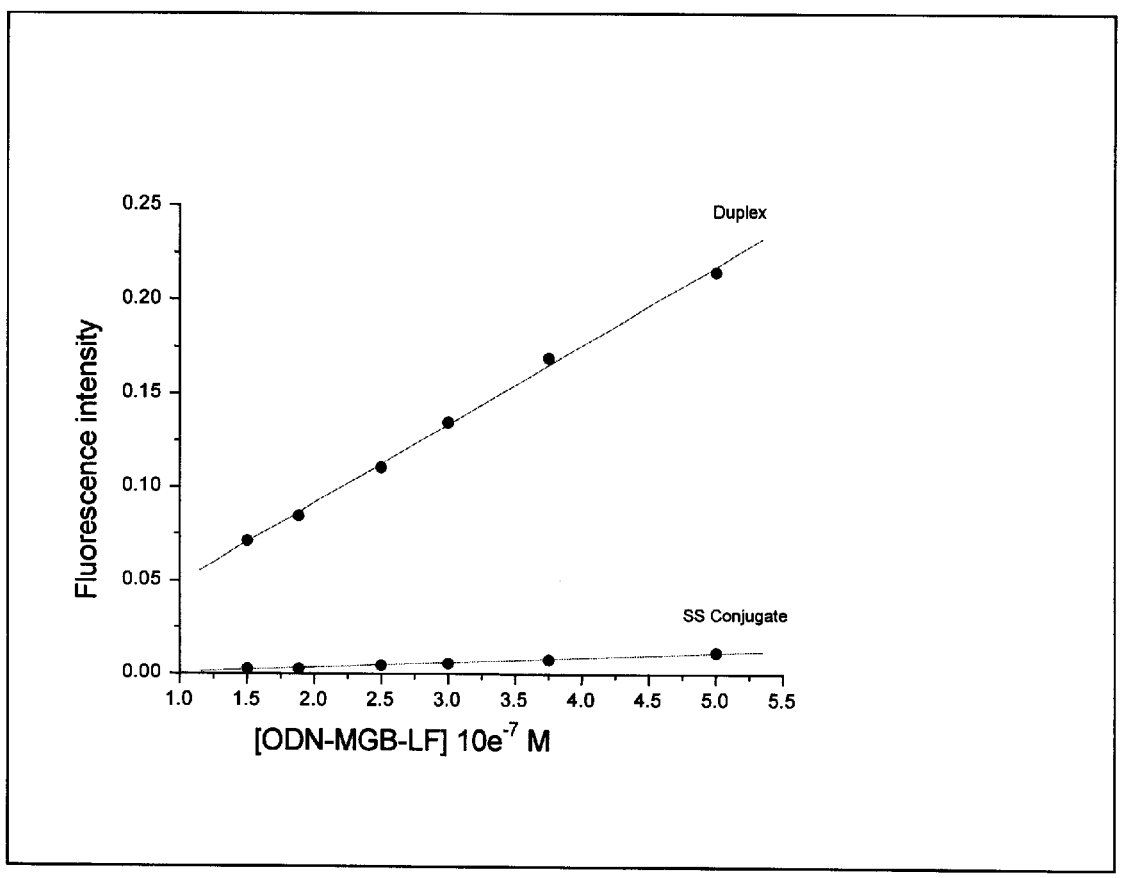
FIG. 2B shows hybridization-triggered fluorescence with a conjugate, TO-MGB-5'-TTCCCGAGCGGC-3' (SEQ ID NO: 2), containing a GC-rich sequence. See Example 1, infra, for hybridization conditions.

Hybridization-triggered fluorescence, using the methods and compositions of the invention, can be obtained for target sequences that are either AT- or GC-rich. FIGS. 2A and 2B provide examples in which a cyanine dye (TO) is used as a latent fluorophore in an ODN-MGB-LF conjugate to detect an AT-rich target sequence (FIG. 2A) and a GC-rich target sequence (FIG. 2B). FIGS. 2A and 2B show that the ODN-MGB-TO conjugate exhibits an increase in fluorescence emission intensity only after specific hybridization with a complementary target sequence.

In the example shown in FIGS. 2A and 2B, restricted rotation about the cyanine-methine bond of the TO molecule is believed to be responsible for the increase in fluorescence quantum yield. Without wishing to be bound by any particular theory, it is thought that restriction of rotation is a result of intercalation of the TO molecule into double-stranded DNA. For latent fluorophores other than TO, binding to DNA can result in restrictions of rotational freedom by other mechanisms, such as major groove or minor groove binding, or by mechanisms resulting from the conjugation of the latent fluorophore to the MGB-ODN and base-pairing of the ODN with its complementary target sequence.

Figure 3A:
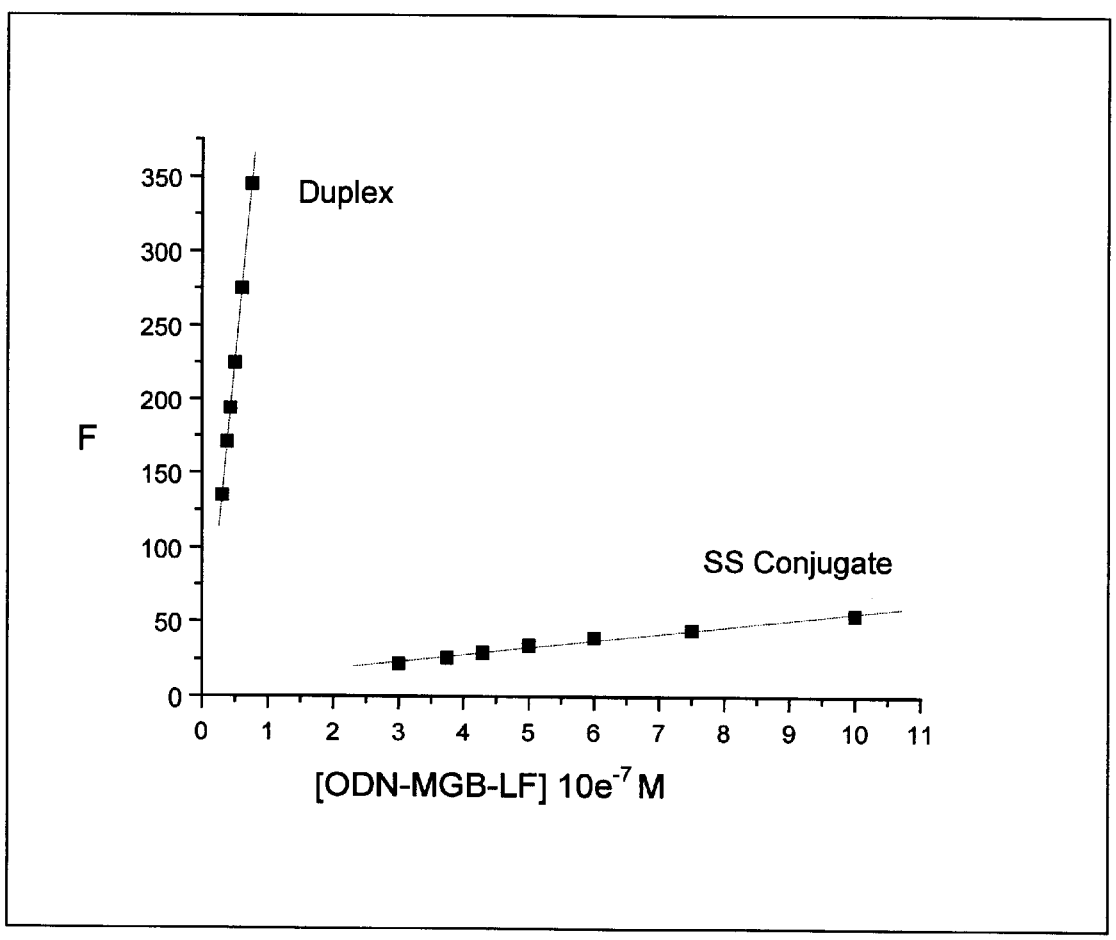
FIG. 3A shows fluorescence of the ODN-MGB-LF conjugate TO-MGB-5'-CAATTTAAAGAAAAGAAG-3' (SEQ ID NO: 3), as a function of its concentration, in the presence of an equimolar concentration of its complementary sequence.
Figure 3B:
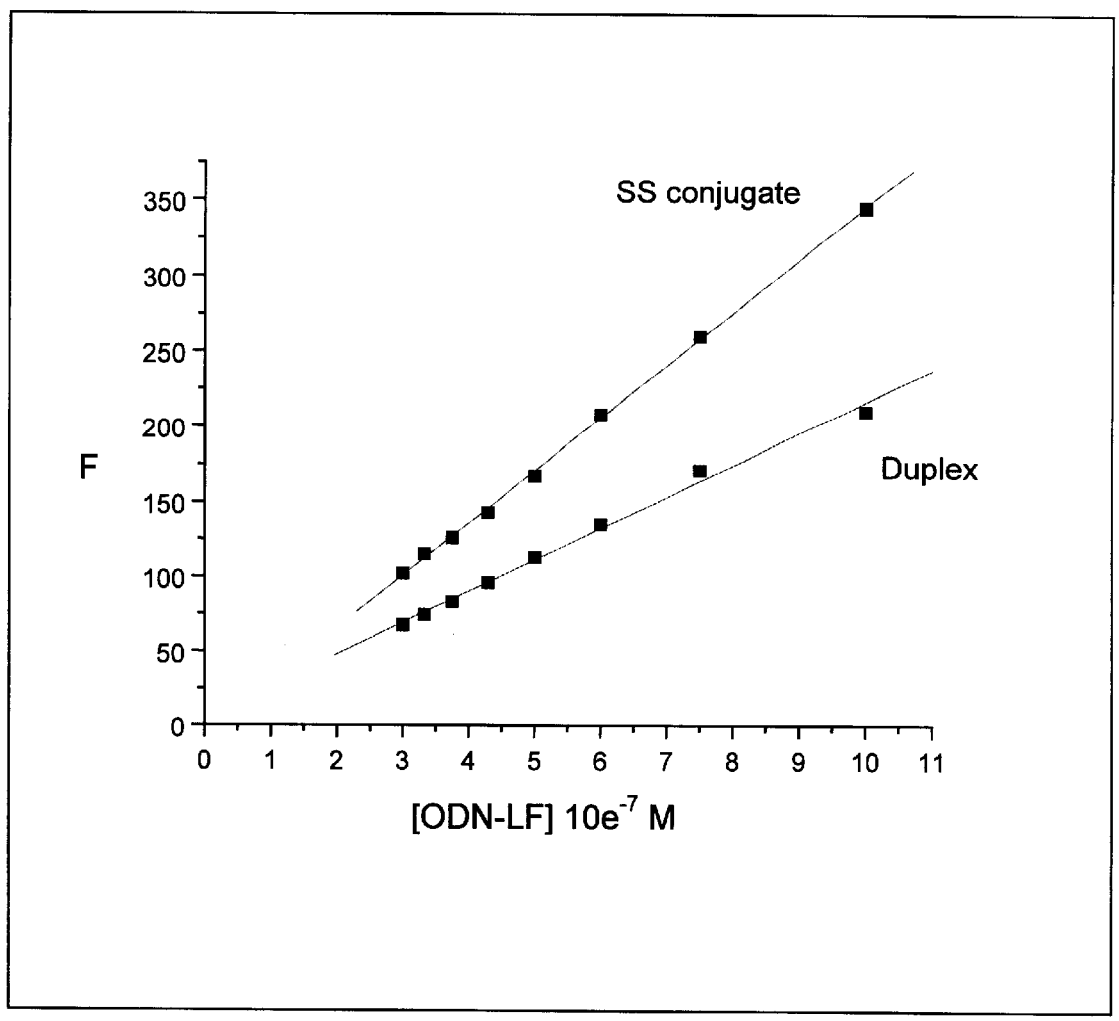
FIG. 3B shows fluorescence of a ODN-TO conjugate, containing the same sequence but lacking a MGB, as a function of its concentration in the presence of an equimolar concentration of its complementary sequence. "F" on the ordinate refers to fluorescence intensity, in arbitrary units. See Example 1, infra, for hybridization conditions.

Attachment of a latent fluorophore to a MGB moiety facilitates the observed increase in fluorescent output by a latent fluorophore following hybridization of an ODN-MGB-LF conjugate to a complementary target sequence. This is demonstrated in FIGS. 3A and 3B, which show changes in fluorescent output for ODN-TO conjugates containing (FIG. 3A) or lacking (FIG. 3B) a MGB as part of the conjugate. Without wishing to be bound by any particular theory, it is thought that the anchoring of the MGB moiety of the conjugate in the minor groove facilitates intercalation by the LF (in this case, the TO moiety) and subsequent fluorescence. Additional mechanisms, such as synergistic interactions between the MGB and the LF, are also possible.

Additional examples of hybridization-triggered fluorescence are presented in Table 2, in which different LFs and different ODNs were evaluated. Hybridizations were conducted with $1 \times 10^{-7}$ M conjugate and a 2-fold molar excess of complementary target sequence in a pH 7.4 phosphate buffer for 5 min at 25° C. (See Example 1 for buffer composition.) Increase in fluorescence yield ("Fluorescence Increase" column of Table) is presented as the ratio of fluorescence emitted by the hybrid between the ODN-MGB-LF conjugate and its target sequence to the fluorescence emitted by unhybridized (i.e., single-stranded) ODN-MGB-LF.

TABLE 2

Hybridization-triggered fluorescence with different ODN-MGB-LF conjugates
Schematic Representation of Fluorophore-MGB-ODN Conjugates

| Conjugate | R1 | R2 | Fluorescence Increase |
|---|---|---|---|
| 1 | (acetyl-pyrroloindole structure) | TTTTTTTTTTTTTTTT | 8.3 |
| 2 | (dansyl-like naphthalene sulfonyl dimethylamino structure) | GAAGTTGCTT (SEQ ID NO: 6) | 3.1 |
| 3 | (dansyl-like naphthalene sulfonyl dimethylamino structure) | GAATTTGCTT (SEQ ID NO: 7) | 4.2 |
| 4 | (dansyl-like naphthalene sulfonyl dimethylamino structure) | TTTTTTTTTT | 8.7 |
| 5 | (extended naphthalene/anthracene sulfonyl dimethylamino structure) | TTTTTTTTTTTTTT | 23 |

Figure 4A:
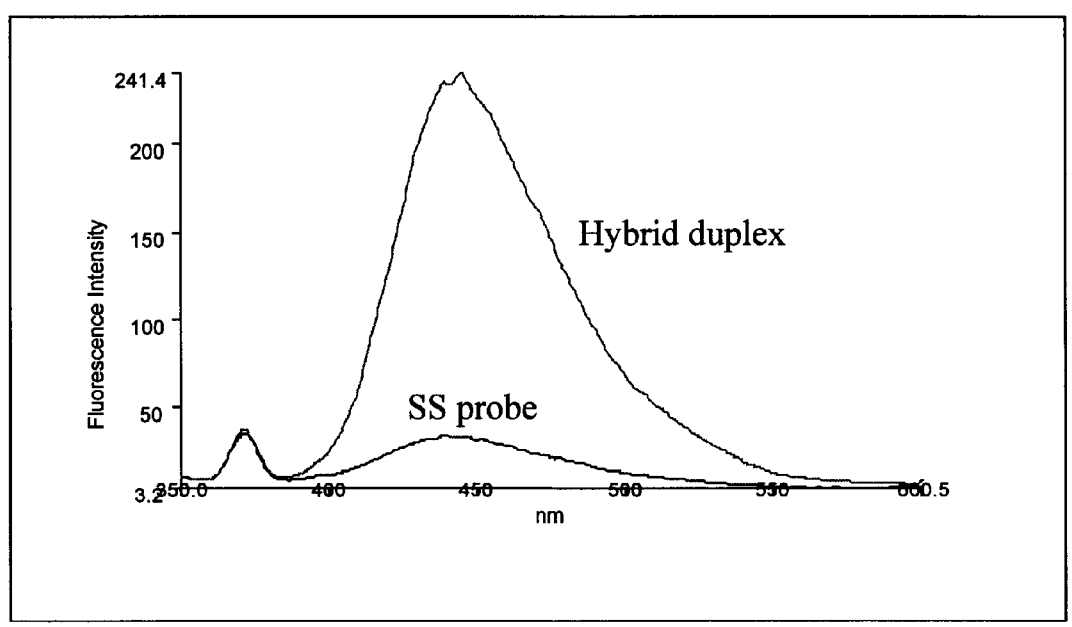
FIG. 4A shows fluorescence spectra of a 15-mer poly dT-MGB-(2-dimethylaminonaphthalene-6-sulfonamide) conjugate at a concentration of $1\times10^{-7}$ M(lower trace, labeled "SS probe") and a hybrid of this probe with a two-fold molar excess of a poly rA target (upper trace, labeled "Hybrid duplex"). Hybridization was conducted in 10 mM phosphate, 0.15 M NaCl, 1 mM EDTA, pH 7.4 for 15 min at 25° C.
Figure 4B:
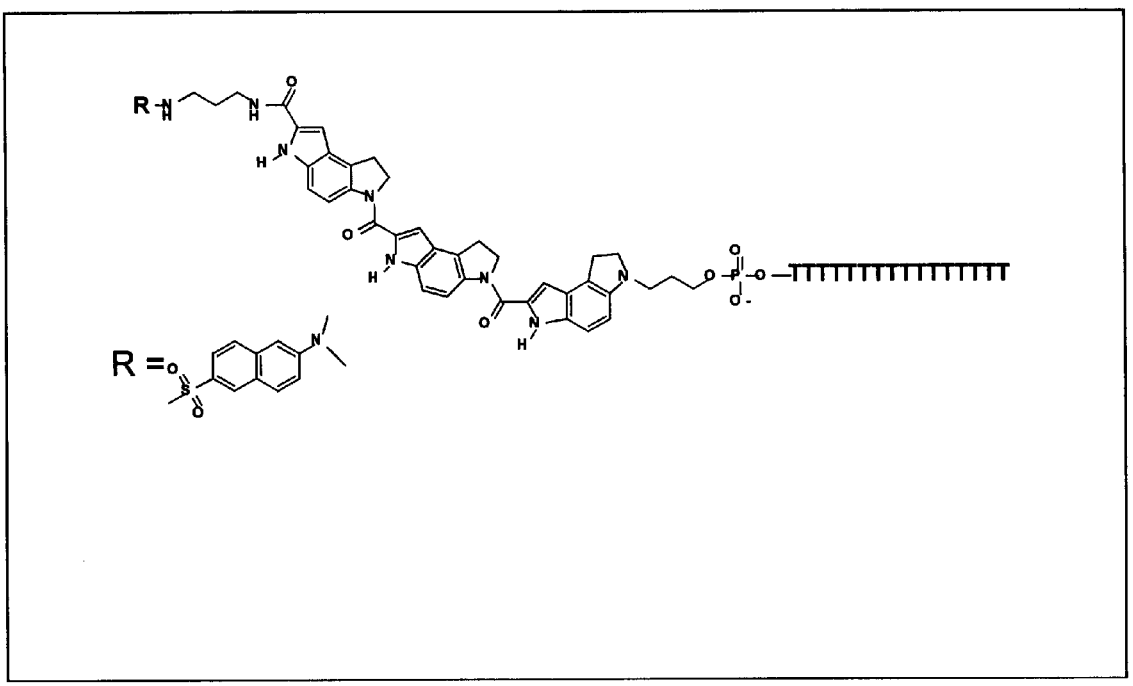
FIG. 4B shows the structure of the conjugate.

An example of hybridization-triggered fluorescence in a DNA-RNA hybrid, using a ODN-MGB-LF conjugate, is provided in FIG. 4. This figure shows that when a poly(dT)$_{15}$-MGB-dansyl conjugate is hybridized to a poly(A) target, an approximately 8-fold increase in fluorescence, compared to unhybridized conjugate, is observed. Hybridization conditions are given in the legend to FIG. 4. This result demonstrates that hybridization-triggered fluorescence can be observed in hybrids between heterologous polynucleotides such as DNA and RNA, and is thus a general phenomenon.

In general, the $T_m$ of a hybrid between an ODN-MGB-LF and its target sequence is higher than the $T_m$ of a hybrid between an unconjugated ODN and the same target sequence, due to the presence of the MGB. See, for example, U.S. Pat. No. 5,801,155. Consequently, at stringencies at which an unconjugated ODN is not able to form hybrids with sequences related to its complementary target sequence (i.e., mismatches), an ODN-MGB-LF may be capable of forming hybrids with such related sequences. Accordingly, ODN-MGB-LF conjugates can be used, not only for detection of a perfectly complementary target sequence, but also for detection of sequences related to a target sequence that is complementary to the ODN portion of the ODN-MGB-LF conjugate as, for example, in the identification of gene families.

ODN-MGB-LF compositions are also useful in methods that involve mismatch discrimination. In this respect, they are similar to previously-described ODN-MGB conjugates, which form highly stable duplexes with perfectly complementary sequences, but more unstable duplexes with target sequences containing a single-nucleotide mismatch with respect to the ODN portion of the conjugate. This property of ODN-MGB conjugates is observed for ODN sequences at least as short as 8 nucleotides. See International Patent Application No. PCT/US99/07487. However, unlike ODN-MGB conjugates, hybrids comprising ODN-MGB-LF conjugates are inherently detectable by virtue of their hybridization-triggered fluorescence.

Figure 5:
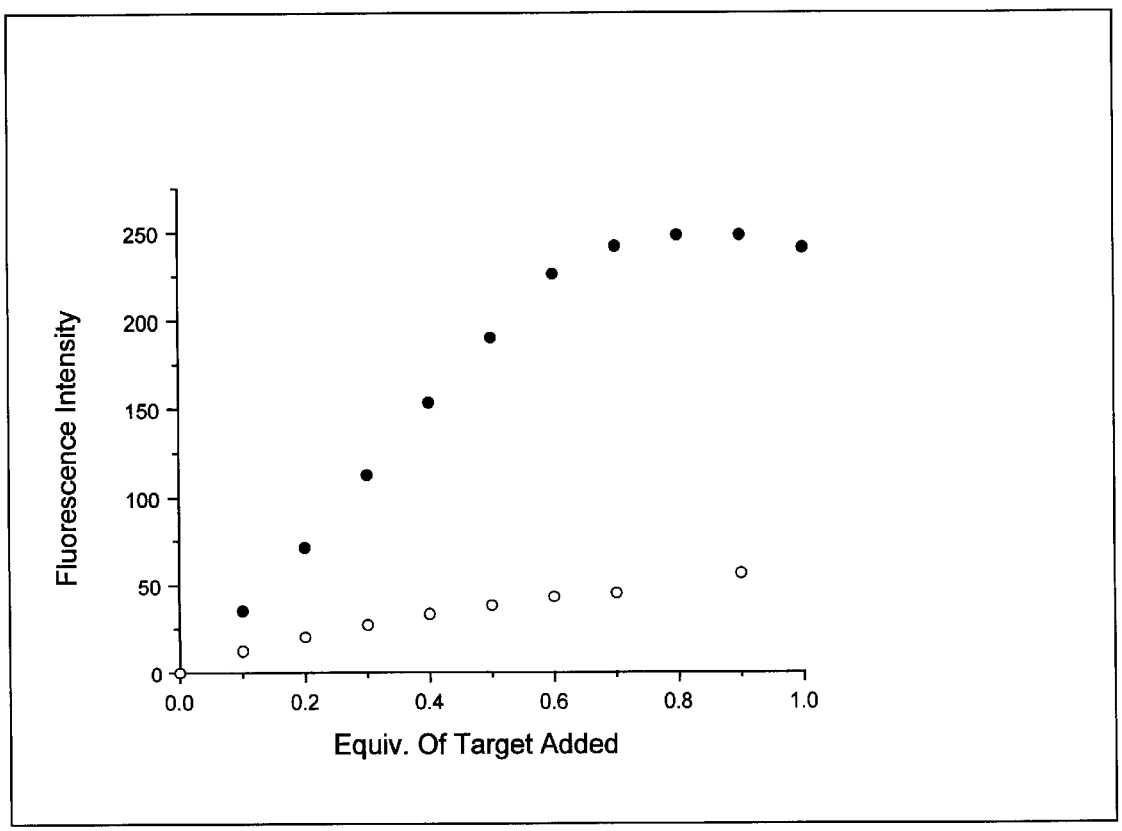
FIG. 5. Discrimination between matched and mismatched target sequences. Fluorescence of conjugate 3 (see Table 2), at a concentration of $6.7\times10^{-7}$ M, was measured as a function of the concentration of its target sequence. In the upper curve (solid circles), the target was perfectly complementary to the ODN portion of the conjugate, having the sequence 5'-TTTCTTAA<u>A</u>ACGAATTT-3' (SEQ ID NO: 4). In the lower curve, the target, 5'-TTTCTTAA<u>C</u>ACGAATTT-3' (SEQ ID NO: 5), had a single-nucleotide mismatch with respect to the ODN portion of the conjugate, as indicated by underlining. Hybridization was conducted in pH 7.4 buffer (10 mM phosphate, 0.15 M NaCl, 1 mM EDTA) at 25 C for 15 min.

Mismatch detection by an ODN-MGB-LF conjugate is exemplified in FIG. 5, wherein it is shown that an ODN-MGB-LF (conjugate 3 of Table 2) does not exhibit substantial fluorescence when it is incubated under hybridization conditions with a sequence having a single-nucleotide mismatch with the ODN portion of the conjugate. Incubation of the same ODN-MGB-LF with a perfectly complementary target sequence under the same conditions, however, as shown in FIG. 5, results in an increase in fluorescence. Hybridization conditions are given in the legend to FIG. 5.

In another experiment, the melting temperatures ($T_m$s) of hybrids between ODN-MGB-LF conjugates, and either perfectly-matched or single-nucleotide mismatched DNA target sequences, were determined. This was accomplished by forming hybrids, gradually heating the hybrids, and plotting -dF/dt (change in fluorescence with respect to time) vs. temperature. The $T_m$ (also known as $T_{max}$) is the temperature at which maximum -dF/dt is observed. Conjugates having an ODN portion of different lengths were tested and the results are provided in Example 8 infra. ODN-MGB-TO conjugates, having oligonucleotide portions between 10 and 18 nucleotides in length, provided excellent discrimination between perfectly matched and mismatched target sequences, with $\Delta T_m$s of 10° C. or greater, where $\Delta T_m$ is the difference in melting temperature between a perfectly-matched hybrid and a hybrid containing a mismatch. See Example 8.

Exemplary Applications for ODN-MGB-LF Conjugates

Methods and compositions of the invention are useful in the detection of specific nucleic acid sequences by hybridization. For the purposes of the invention, the term "hybridization" refers to the interaction of two or more nucleic acids to form a stable multi-stranded structure. For two or more nucleic acids to interact by "specific hybridization," the multi-stranded structure formed therefrom can be a duplex, triplex, or any other higher order structure wherein the interaction is mediated, at least in part, by specific base-pairing. Base-pairing includes so-called Watson-Crick pairing, involved in duplex formation, as well as Hoogsteen and reverse Hoogsteen pairing, which are involved in triplex formation. Nucleic acids, either target nucleic acids or the oligonucleotide portion of a ODN-MGB-LF, can be DNA, RNA, modified DNA, modified RNA, or any modified nucleic acid or nucleic acid analogue known to one of skill in the art. Nucleic acid analogues include, but are not limited to, peptide or polyamide nucleic acids (Nielsen et al. (1991) *Science* 254:1497–1500), bicyclo nucleic acids (Bolli et al. (1996) *Nucleic Acids Res.* 24:4660–4667) 1-α-arabinofuranosyl-containing oligonucleotides (U.S. Pat. No. 5,177,196) and oligonucleotide analogues with sulfamate linkages (U.S. Pat. No. 5,470,967). Nucleic acids can also be chimeric molecules containing different types of nucleotides and/or nucleotide analogues within the same molecule such as, for example, PNA/DNA chimeras. See, for example, Nielsen, supra and Koch, supra.

ODN-MGB-LF conjugates can be used as probes, in which their hybridization to a target sequence is detected, or as primers, in which their hybridization to a target sequence is followed by polynucleotide synthesis initiated from the 3' terminus of the oligonucleotide portion of the conjugate, and the synthesized product (i.e., the extension product) is detected.

A target sequence refers to a nucleotide sequence in a nucleic acid which comprises a site of specific hybridization for a probe or a primer. Target sequences can be found in any nucleic acid including, but not limited to, genomic DNA, cDNA and RNA, and can comprise a wild-type gene sequence, a mutant gene sequence, a non-coding sequence, a regulatory sequence, etc. A target sequence will generally be less than about 100 nucleotides, preferably less than about 50 nucleotides, and more preferably, less than about 25 nucleotides in length.

Hybridization of a probe and/or a primer to a target sequence to form a duplex proceeds according to well-known and art-recognized base-pairing properties, such that adenine base-pairs with thymine or uracil, and guanine base-pairs with cytosine. The property of a nucleotide that allows it to base-pair with a second nucleotide is called complementarity. Thus, adenine is complementary to both thymine and uracil, and vice versa; similarly, guanine is complementary to cytosine and vice versa. An oligonucleotide which is complementary along its entire length with a target sequence is said to be perfectly complementary, perfectly matched, or fully complementary to the target sequence, and vice versa. An oligonucleotide and its target sequence can have related sequences, wherein the majority of bases in the two sequences are complementary, but one or more bases are deleted, inserted, transposed or noncomplementary (i.e., mismatched). In such a case, the sequences can be said to be substantially complementary to one another, if their degree of complementarity is sufficient to allow detectable hybrid formation. The ability to detect a hybrid will depend upon the stringency of hybridization, as is known to those of skill in the art. See infra. If the sequences of an oligonucleotide and a target sequence are such that they are complementary at all nucleotide positions except one, the oligonucleotide and the target sequence have a single nucleotide mismatch with respect to each other.

Conditions for hybridization are well-known to those of skill in the art and can be varied within relatively wide limits. Hybridization stringency refers to the degree to which hybridization conditions disfavor the formation of hybrids containing mismatched nucleotides, thereby promoting the formation of perfectly matched hybrids or hybrids containing fewer mismatches; with higher stringency correlated with a lower tolerance for mismatched hybrids. Factors that affect the stringency of hybridization include, but are not limited to, temperature, pH, ionic strength, and concentration of organic solvents such as formamide and dimethylsulfoxide. As is well known to those of skill in the art, hybridization stringency is increased by higher temperatures and/or lower ionic strengths. See, for example, Ausubel et al., supra; Sambrook et al., supra; M. A. Innis et al. (eds.) PCR Protocols, Academic Press, San Diego, 1990; B. D. Hames et al. (eds.) Nucleic Acid Hybridisation: A Practical Approach, IRL Press, Oxford, 1985; and van Ness et al., (1991) *Nucleic Acids Res.* 19:5143–5151. The degree of stringency can be adjusted not only during a hybridization reaction, but also in post-hybridization washes, as is known to those of skill in the art.

Thus, in the formation of hybrids between an ODN-MGB-LF and its target sequence, the ODN-MGB-LF can be incubated in solution, together with a polynucleotide containing the target sequence, under conditions of temperature, ionic strength, pH, etc, that favor specific hybridization (i.e., duplex or triplex formation mediated by base-pairing). Alternatively, the ODN-MGB-LF can be immobilized on a solid support, which is contacted with a solution potentially containing a polynucleotide comprising a target sequence. In yet another embodiment a population of polynucleotides, one or more of which potentially comprises a target sequence, is immobilized on a solid support, which is contacted with a solution containing one or more ODN-MGB-LF conjugates. A polynucleotide is a polymer of nucleotides and is not limited with respect to length. Polynucleotides can comprise DNA, RNA, and DNA and/or RNA analogues. A polynucleotide can also comprise multiple types of nucleotides or nucleotide analogues, i.e., DNA/RNA or DNA/PNA chimeras.

Hybridization conditions are chosen, in some circumstances, to favor hybridization between two nucleic acids having perfectly-matched sequences, as compared to a pair of nucleic acids having one or more mismatches in the hybridizing sequence (i.e., high stringency conditions). In other circumstances, hybridization conditions of reduced stringency can be chosen to allow hybridization between mismatched sequences.

The degree of hybridization of an oligonucleotide or oligonucleotide conjugate to a target sequence, also known as hybridization strength, is determined by methods that are well-known in the art. A preferred method is to determine the melting temperature ($T_m$) of the hybrid duplex. This can be accomplished, for example, by subjecting a duplex to gradually increasing temperature and monitoring the denaturation of the duplex, for example, by absorbance of ultraviolet light, since UV absorption increases with the unstacking of base pairs that accompanies denaturation. $T_m$ can be defined as the temperature midpoint of the transition in ultraviolet absorbance that accompanies denaturation. Another quantitative indicator of hybridization strength is $T_{max}$, which is the temperature at which the maximum rate of unpairing of bases with respect to time is observed, as a hybrid is subjected to successively increasing temperature. Unpairing of bases can be measured, for example, by changes in UV absorbance or by changes in fluorescence of a hybrid containing an ODN-MGB-LF. A higher $T_{max}$ correlates with increased hybridization strength. Further description of $T_{max}$ determination is presented in Example 8, infra.

One method for distinguishing between two duplexes, if their $T_m$s are known, is to conduct hybridization at a temperature that is below the $T_m$ of the desired duplex and above the $T_m$ of an undesired duplex. In this case, determination of the degree of hybridization is accomplished simply by testing for the presence of hybridized probe.

Thus, in one embodiment, MGB-ODN-LF conjugates are used as probes or primers for detection of specific nucleic acid sequences. Detection is accomplished according to techniques known to those of skill in the art including, but not limited to, solution hybridization, blot hybridization, in situ hybridization, nuclease protection, cDNA synthesis, priming, and amplification. Amplification technology includes both target amplification methods and signal amplification techniques.

Target amplification methods include, for example, polymerase chain reactions (PCR), NASBA, SSSR, rolling circle amplification (Lizardi et al. (1998) *Nature Genet.* 19:225–232), cleavase-based amplification (Sander et al. (1999) *Electrophoresis* 20:1131–1140) and related amplification technologies. In the various target amplification methods, ODN-MGB-LF conjugates can be used as either primers for the synthesis of amplification products or as probes to detect the amplification products.

Signal amplification techniques involve hybridization of a probe, having two portions, to a target sequence. A first portion of the probe is complementary to a target sequence. A second portion of the probe has a plurality of sequence units, each of which is complementary to a labeled oligonucleotide; alternatively, the second portion is complementary to another probe having a plurality of sequence units, each of which is complementary to a labeled oligonucleotide. See, for example, U.S. Pat. Nos. 5,124,246; 5,594,118 and 5,902,724. The compositions and methods of the invention, when used in conjunction with signal amplification methods, for example as labeled oligonucleotides, provide even greater sensitivity by virtue of their capacity for hybridization triggered fluorescence.

Additional applications include gene expression analysis, single-nucleotide polymorphism analysis and sequence-based identification of organisms, including infectious organisms, using RT-PCR, arrays, and array-PCR. Additional detection systems are disclosed in International Patent Application Nos. PCT/US99/07487 and PCT/US99/07492, the disclosures of which are incorporated herein by reference.

Hybridization-triggered fluorescence, according to the invention, can be used in any system in which detection of a hybrid duplex or triplex is of interest, by using the appropriate ODN-MGB-LF conjugate as a primer or a probe. Non-limiting examples include:

1) Quantitation of a particular nucleic acid sequence in the presence of other similar nucleic acid sequences,
2) Qualitative discrimination between two sequences having a single nucleotide difference, and
3) Detection of a very small amount of a specific DNA sequence.

An additional application of ODN-MGB-LF conjugates is in real-time detection of PCR products. Wittwer et al. (1997) *Biotechniques* 22:176–81. Under appropriate conditions, an ODN-MGB-LF conjugate used as a PCR primer provides single-nucleotide mismatch discrimination in real time. See FIG. 6 and Example 9, infra.

A particular advantage of the hybridization-triggered fluorescent probes is in the area of multiplex detection (i.e., detection and quantitation of more than one PCR product in the same reaction vessel). For example, for two distinct target sequences, one complementary to ODN-A and the other complementary to ODN-B, conjugation of, for example, thiazole orange to ODN-A and thiazole blue to ODN-B allows simultaneous detection and quantitation of both target sequences. Additional latent fluorophores, having distinct emission maxima, can be conjugated to additional oligonucleotides, to enable multiplex detection of additional distinct target sequences. The potential for multiplex detection using the methods and compositions of the invention is limited only by the resolving power of the fluorescent detection system.

The methods and compositions of the invention are also useful in procedures that utilize arrays of oligonucleotides, such as sequencing by hybridization and array-based analysis of gene expression. In these procedures, an ordered array of oligonucleotides of different sequences is used as a platform for hybridization to one or more test polynucleotides, nucleic acids or nucleic acid populations. Generally, an array comprises a set of distinct addresses, each of which contains an oligonucleotide of distinct sequence. Determination of the oligonucleotides that are hybridized and alignment of their sequences, if known, allows reconstruction of the sequence of the test polynucleotide. See, for example, U.S. Pat. Nos. 5,492,806; 5,525,464; 5,556,752; and PCT Publications WO 92/10588 and WO 96/17957. Materials for construction of arrays include, but are not limited to, nitrocellulose, glass, silicon wafers, optical fibers and other materials suitable for construction of arrays such as are known to those of skill in the art.

In a preferred array method, an ODN-MGB-LF conjugate is immobilized on a solid surface, where it serves as a capture probe and/or an extension primer. Hybridization and/or extension results in fluorescence. Various methods for immobilization of ODN conjugates to solid surfaces are known in the art. See, for example, Ramsay (1998) *Nature Biotechnol* 16:40–44; U.S. Pat. No. 5,412,087; U.S. Pat. No. 5,424,186; WO 95/11748 and EP 373,203.

ODN-MGB-LF conjugates are particularly advantageous for use as immobilized probes in various types of array-based technology, because assays can be conducted without the necessity for labeling target nucleic acids. Hybridization of a target nucleic acid to an immobilized ODN-MGB-LF on an array results in the immediate generation of a fluorescent signal at the site of the hybridized probe, without the need for any type of post-hybridization labeling or detection steps.

The following examples are provided to illustrate, but not to limit, the invention.

EXAMPLES

General Experimental

Thin-layer chromatography was run on silica gel 60 F-254 (EM Reagents) aluminum-backed plates. $^1$H NMR spectra were obtained at 300 MHz on a Varian VXR-300 spectrometer in DMSO-$d_6$. Elemental analyses were performed by Quantitative Technologies Inc. (Boundbrook, N.J.). Mass spectrometry was performed by Mass Consortium (San Diego, Calif.). All procedures were carried out at room temperature unless otherwise specified.

Example 1

Steady-State Fluorescence Measurements

Fluorescence spectra were recorded on a Perkin Elmer model MPF-44A, or a Perkin Elmer model LS50B fluorescence spectrophotometer at ambient temperature. A Xenon lamp was used as the radiation source employing an excitation wavelength appropriate for a particular dye (e.g., 485–507 nm for thiazole orange).

For the experiments shown in FIGS. 2 and 3, concentrations of thiazole orange conjugates were typically varied in the range of $3\times10^{-8}$ M to $5\times10^{-7}$ M in pH 7.2 buffer (10 mM sodium cacodylate, 0.2 M NaCl, 1 mM EDTA), by serial dilution of a $5\times10^{-7}$ M solution. For duplex measurements, an equal molar ratio of target sequence was added to a $5\times10^{-7}$ M solution of conjugate, followed by a 15 min incubation at 25° C. Serial dilutions were then performed as described above.

Fluorescence spectra of conjugates containing an environment-sensitive fluorophore were typically taken at a concentration of $1\times10^{-7}$ M in pH 7.4 buffer (10 mM phosphate, 0.15 M NaCl, 1 mM EDTA). Hybrids were formed by adding 1–2 equivalents of target sequence.

Example 2

Synthesis of oligonucleotides (ODNs)

All ODNs were prepared from 1 μmol appropriate CPG support on an ABI 394 synthesizer using the protocol supplied by the manufacturer. Protected β-cyanoethyl phosphoramidites of 2'-deoxyribo and 2'-O-methylribonucleotides, CPG supports, deblocking solutions, cap reagents, oxidizing solutions and tetrazole solutions were purchased from Glen Research. 5'-Aminohexyl modifications were introduced using an N-(4-monomethoxytrityl)-6-amino-1-hexanol phosphoramidite linker (Glen Research). 3'-Aminohexyl and 3'-hexanol modifications were introduced using a modified CPG prepared as previously described. Petrie et al (1992) *Bioconjugate Chem.* 3:85–87; and U.S. Pat. No. 5,212,667. All other general methods employed for preparative HPLC purification, detritylation and butanol precipitation were carried out as described. Reed et al. (1991) *Bioconjugate Chem.* 2:217–225. Purified oligonucleotides were analyzed by C-18 HPLC (column 250×4.6 mm) in a gradient of 0—30% acetonitrile in 0.1 M triethylamine acetate buffer, pH 7.0, over 20 min at a flow rate of 2 ml/min. Pump control and data processing were performed using a Rainin Dynamax chromatographic software package on a Macintosh computer. ODN purity was assessed by capillary gel electrophoresis (CGE) with a P/ACE™ 2000 Series equipped with an eCAP™ cartridge (Beckman, Fullerton, Calif.). Oligonucleotides were >95% pure by C-18 HPLC and showed one major peak on CGE.

Example 3

Synthesis of p-nitrophenyl Carbonate-activated Latent Fluorophores 1-(3-Hydroxypropyl)-4-methylquinolinium bromide (3). A solution of lepidine (0.49 g, 3.43 mmol) and 3-bromo-1-propanol (3.1 ml, 34 mmol) in 3.0 ml of 1,4-dioxane was refluxed for 17 h. The solution was cooled to room temperature and then diluted with 30 ml of ether. The product separated as an oil and the ether layer was discarded. The oil was crystallized from methylene chloride: 367-mg (38%) yield; TLC (5:3:2, n-butanol/water/acetic acid), Rf=0.40; $^1$H NMR δ 9.39 (1H, d, J=6.0 Hz, aromatic), 8.57 (2H, t, J=9.1 Hz, aromatic), 8.27 (1H, t, J=7.8 Hz, aromatic), 8.05 (2H, m, aromatic), 5.08 (2H, t, J=7.1 Hz, methylene), 4.81 (1H, t, J=4.9 Hz, hydroxyl), 3.51 (2H, m, methylene), 3.01 (3H, s, 4-methyl), 2.11 (2H, m, methylene). Anal. Calcd. For $C_{13}H_{16}BrNO$ 0.3 $H_2O$; C, 54.29; H, 5.82; N, 4.87. Found C, 53.92; H, 5.43; N, 4.67.

1-(3-Hydroxypropyl)-thiazole orange (4). To a solution of 3-methyl-2-thiomethyl-benzothiazolium iodide (0.38 g, 1.22 mmol) and 3 (0.34 g, 1.22 mmol) in 40 ml of absolute ethanol was added triethylamine (0.26 ml). The solution was stirred for 30 minutes at room temperature and the crystals that formed were filtered, rinsed with ethanol and dried: 283 mg. yield; TLC (5:3:2, n-butanol/water/acetic acid), $R_f$=052.; $^1$H NMR δ 8.81 (1H, d, J=8.3 Hz), 8.61 (1H, d, J=7.4 Hz), 8.14 (1H, d, J=8.6 Hz), 8.02 (2H, m), 7.77 (2H, m), 7.61 (1H, t, J=7.4 Hz), 7.40 (2H, m), 6.93 (1H, s), 4.82 (1H, t, J=4.7 H, hydroxyl), 4.66 (2H, t, J=6.5 Hz, methylene), 4.02 (3H, s, methyl), 3.50 (2H, m, methylene), 2.01 (2H, m, methylene). Anal. Calcd. For $C_{21}H_{21}IN_2OS.0.95\ H_2O$; C, 51.11; H, 4.68; N, 5.68. Found C, 50.76; H, 4.23; N, 5.42.

4-Nitrophenyl carbonate derivative (5). 4-Nitrophenyl chloroformate (48 mg, 0.240 mmol) and 4 (50 mg, 0.120 mmol) were stirred in 6.0 ml of anhydrous pyridine at 70° C. for 2 h. Another portion of 4-nitrophenyl chloroformate (48 mg) was added and stirring was continued for another hour. The solution was evaporated to dryness and the residue was crystallized from DMF-THF. The red solid was filtered, rinsed with THF and dried: 29 mg yield; TLC (5:3:2, n-butanol/water/acetic acid), $R_f$=0.58; $^1$H NMR δ 8.81 (1H, d, J=8.5 Hz), 8.60 (1H, d, J=7.4 Hz), 8.27–7.97 (5H, m), 7.77 (2H, m), 7.62 (1H, t, J=7.4 Hz), 7.50–7.32 (4H, m), 6.93 (1H, s), 4.70 (2H, t, J=6.8 Hz, methylene), 4.03 (3H, s, methyl), 3.79 (2H, t, J=6.0 Hz, methylene), 2.33 (2H, m, methylene). HRMS (FAB) m/e 514.1416 M$^+$, calcd for $C_{28}H_{24}N_3O_5S$, 514.1437.

Example 4

Synthesis of 2,3,5,6-tetrafluorophenyl 3-[(3-{[3-(6-{[(4-methoxyphenyl)diphenylmethyl]amino}hexanoyl)pyrrolo[4,5-e]indolin-7-yl]carbonyl}pyrrolo[4,5-e]indolin-7-yl)carbonyl]pyrrolo[4,5-e]indoline-7-carboxylate (12) according to Reactions Scheme 4

6-{[(4-methoxyphenyl)diphenylmethyl]amino}hexanoic acid, triethylammonium salt (6). A suspension of 6-aminohexanoic acid (5.0 g, 38 mmol) in 50 ml of anhydrous pyridine was treated with p-anisylchlorodiphenylmethane-MMTrCl (6.0 g, 19.4 mmol). After being stirred for 24 hours at room temperature, the mixture was concentrated, and the residue, a viscous liquid, was partitioned between water and $CH_2Cl_2$. The organic layer was washed with water and dried over anhydrous sodium sulfate. The crude product was chromatographed on silica eluting with 5% MeOH, 0.5% triethylamine in $CH_2Cl_2$. Concentration of the proper fractions and drying under vacuum afforded 2.2 g (22% yield) of the desired MMTr-derivative as a pale-yellow, viscous oil.

2,3,5,6-tetrafluorophenyl 6-{[(4-methoxyphenyl)diphenylmethyl]amino}hexanoate (7). The acid 6 obtained as described above (2.2 g, 4.4 mmol) was dissolved in anhydrous $CH_2Cl_2$ and treated with 1 ml of triethylamine followed by 0.8 ml of 2,3,5,6-tetrafluorophenyltrifluoroacetate. After being kept at room temperature for 30 min, the reaction was concentrated to an oil (crude 7), which then was re-suspended in 20% ethyl acetate/80%hexane and applied to a silica gel column. Elution with 15% ethyl acetate/85% hexane and concentration of the pure product fractions afforded 2.0 g (82%) of the TFP ester (7) as a colorless, viscous oil.

Methyl 3-(6-{[1-(4-methoxyphenyl)-2-methylene-1-phenylbut-3-enyl]amino}hexanoyl)pyrrolo[4,5-e]indoline-7-carboxylate (8). A solution of 7 (0.6 g, 1.1 mmol) was combined with 0.24 g (1.2 mmol) methyl pyrrolo[4,5-e]indoline-7-carboxylate (Boger et al, supra) and 0.1 ml triethylamine in 5 ml of anhydrous $CH_2Cl_2$. The mixture was kept at room temperature for 15 h and concentrated under vacuum. The resultant solid, which was the desired product, was washed with 50% ethyl acetate/50%hexane to remove unreacted starting materials and 2,3,5,6-tetrafluorophenol. Drying under vacuum afforded 0.51 g (77%) of the title compound as a pale-yellow, crystalline solid.

3-(6-{[1-(4-methoxyphenyl)-2-methylene-1-phenylbut-3-enyl]amino}hexanoyl)pyrrolo[4,5-e]indoline-7-carboxylic acid (9). A mixture of 8 (0.47 g, 0.78 mmol), THF (9 ml), MeOH (6 ml) and 4M LiOH (3 ml) was stirred at 55° C. for 1 h. The resultant solution was cooled to give a white precipitate, the Li salt of the product. The solid was triturated with a small amount of cold 10% citric acid and filtered off. Washing with water and drying under vacuum gave 0.43 g (94%) of 9 as a white solid.

Methyl 3-[(3-{[3-(6-{[(2E)-1-(4-methoxyphenyl)-2-methyl-1-phenylpenta-2,4-dienyl]amino}hexanoyl)pyrrolo[4,5-e]indolin-7-yl]carbonyl}pyrrolo[4,5-e]indolin-7-yl)carbonyl]pyrrolo[4,5-e]indoline-7-carboxylate (10). To a solution of 9 (213 mg, 0.36 mmol) and methyl 3-(pyrrolo[4,5-e]indolin-7-ylcarbonyl)pyrrolo[4,5-e]indoline-7-carboxylate (which had been prepared by TFA deprotection of 182 mg of the corresponding t-Boc precursor, Boger et al., supra) in 50 ml of anhydrous DMF was added EDC (200 mg). The reaction was stirred for 20 h 25° C. The resultant precipitate was collected by filtration, then washed with MeOH and ether. Drying under vacuum afforded 313 mg (90%) of the desired product as an off-white solid.

3-[(3-{[3-(6-{[(2E)-1-(4-methoxyphenyl)-2-methyl-1-phenylpenta-2,4-dienyl]amino}hexanoyl)pyrrolo[4,5-e]indolin-7-yl]carbonyl}pyrrolo[4,5-e]indolin-7-yl)carbonyl]pyrrolo[4,5-e]indoline-7-carboxylic acid (11). A suspension of 10 (270 mg, 0.28 mmol) in a mixture of THF (6 ml), MeOH (4 ml) and 4M LiOH (2 ml) was stirred at 55° C. for 30 h. The reaction was cooled and neutralized to pH 6 with cold 10% citric acid. Insoluble material was collected by filtration and washed with water, MeOH and ether. Drying under vacuum afforded 160 mg (60%) of the title compound 11. By HPLC analysis this product contained ~5% of unreacted 10. The crude acid was used in the next step without additional purification.

2,3,5,6-tetrafluorophenyl 3-[(3-{[3-(6-{[(4-methoxyphenyl)diphenylmethyl]amino}hexanoyl)pyrrolo[4,5-e]indolin-7-yl]carbonyl}pyrrolo[4,5-e]indolin-7-yl)carbonyl]pyrrolo[4,5-e]indoline-7-carboxylate (12). To a suspension of 11 (153 mg, 0.16 mmol) in 5 ml of anhydrous DMF were added triethylamine (0.3 ml) and tetrafluorophenyl trifluoroacetate (TFP-TFA, 0.2 ml). The mixture was stirred for about 1 h at 25° C. to give an almost clear solution. The solution was filtered and concentrated under vacuum to an oil. The oil was triturated with methanol to produce a precipitate of the desired TFP ester 12. It was collected by filtration, washed with MeOH then ether, and dried. Yield was 154 mg (90%). This product was ~90% pure by HPLC analysis. No further purification was attempted due to its poor solubility.

Example 5

Synthesis of an ODN-CDPI$_3$-thiazole Orange conjugate (14) According to Reaction Scheme 5

5'-hexylamine modified 15-mer ODNs were prepared and the 5'-MMT group was removed on the synthesizer, using standard conditions. The 5'-hexylamine modified ODN was reacted with the TFP activated 12, then deprotected with aqueous TFA to yield the ODN-MGB conjugate 13. This conjugate was purified by reverse phase HPLC using triethylammonium acetate/acetonitrile and the desired fraction was dried on a centrifugal evaporator (SpeedVac). The residue was dissolved in 20 µl of dry DMSO. To determine the concentration, 1 µl was removed and precipitated from 2% sodium perchlorate. The pellet was washed with acetone, then dried and dissolved in water. Concentration of the initial DMSO solution was determined by $A_{260}$ to be 1.68 mM, using a calculated extinction coefficient for the CDPI$_3$-amine-ODN conjugate of $\epsilon=255,000$ M$^{-1}$ cm$^{-1}$.

15 µl of the DMSO solution of the ODN-CDPI$_3$ conjugate (25.2 nmol) was treated with 1 mg (2 µmol) of the 4-nitrophenyl carbonate derivative of thiazole orange (5) and 5 µl of triethylamine. After shaking for 16 h at room temperature, the crude conjugate was precipitated from 1 ml of 2% sodium perchlorate. The orange pellet was washed with acetone, dried on a SpeedVac and dissolved in 100 µl water. The conjugate (14) was purified by reverse-phase HPLC using triethylammonium acetate/acetonitrile, the fraction containing the conjugate was concentrated to 0.1 ml with butanol, and the conjugate was precipitated with 2% sodium perchlorate. The orange pellet was washed with acetone, dried on a SpeedVac, and dissolved in 50 µl water to give a 0.43 mM solution. An absorbance spectrum showed distinctive absorbances due to the ODN (260 nm), CDPI$_3$ (350 nm) and thiazole orange (500 nm).

Example 6

Synthesis of CPG-CDPI$_3$ Derivative (23) According to Reaction Scheme 7

4-nitrophenyl {2-[(2-hydroxyethyl)sulfonyl] ethoxy}formate (18). A solution of 2,2'-sulfonyldiethanol (4.85 g, 39.75 mmol) andp-nitrophenyl chloroformate (2.0 g, 9.92 mmol), in 20 ml of dry pyridine, was stirred for 2 h at room temperature and then evaporated to dryness. The residue was dissolved in 350 ml of ethyl acetate and washed with water (4×100 ml). The organic solution was dried over sodium sulfate, filtered and evaporated. The crude product was purified by silica gel chromatography, eluting with ethyl acetate. The pure product fractions were pooled and evaporated affording an oil: 0.68 g (22%) yield.

2-({2-[N-(3-{[(4-methoxyphenyl)diphenylmethyl] amino}propyl)carbamoyloxy]-ethyl}sulfonyl)ethyl (4-nitrophenoxy)formate (20). A solution of 18 (0.68 g, 2.13 mmol) and (3-aminopropyl)[(4-methoxyphenyl) diphenylmethyl]amine (0.89 g, 2.56 mmol) was stirred at 40° C. for 30 min. p-nitrophenyl chlorofornate (0.62 g, 3.08 mmol) was added and stirring was continued for an additional 2 h. The solution was diluted with ethyl acetate (350 ml), washed with water (300 ml) and then dried over sodium sulfate and evaporated. The residue was purified by silica gel chromatography eluting with a gradient of 40–100% ethyl acetate in hexane. The pure product fractions were evaporated affording a foam: 351 mg of 20 (35%) yield; $^1$H NMR (DMSO-d$_6$) δ 8.32 (2H, d, J=9.2 Hz, aromatic), 7.56 (1H, d, J=9.2 Hz, aromatic), 7.37 (4H, d, J=7.4 Hz, aromatic), 7.29–7.15 (8H, m, aromatic), 6.83 (2H, d, J=8.9 Hz, aromatic), 4.61 (2H, t, J=5.5 Hz, CH$_2$), 4.29 (2H, t, J=6.0 Hz, CH$_2$), 3.71 (3H, s, methoxy), 3.67 (2H, t, J=5.7 Hz, CH$_2$), 3.51 (2H, t, J=5.8 Hz, CH$_2$), 3.07 (2H, m, CH$_2$), 1.93 (2H, m, CH$_2$), 1.59 (2H, m, CH$_2$).

Synthesis of CPG derivative 21. A mixture of 20 (325 mg, 0.47 mmol) and long chain alkyl amino CPG (5.9 g) was swirled in 24 ml of dry pyridine for 20 h at 25° C. Acetic anhydride (20 ml) was added and the mixture was swirled for an hour at 25° C. and then filtered. The glass beads 21 were rinsed generously with dimethylformamide and ethyl acetate and dried under vacuum.

Synthesis of CPG-CDPI$_2$-derivative (22). A portion of beads 21 (1.5 g) was deprotected by suspending the beads in 3% trifluoroacetic acid in methylene chloride for 5 min. and then filtered. This process was repeated twice. On the third filtration step the filtrate was no longer colored. The beads were rinsed with methylene chloride and then with 50 ml of a solution of 5% triethylamine in acetonitrile, followed by rinses with pure acetonitrile and then ether.

The deprotected beads were mixed with activated ester 24 (140 mg, 0.22 mmol) in 6.0 ml of pyridine/DMF (1:1 v/v) and the mixture was swirled for 18 h at room temperature. Activated ester 24 was prepared according to Lukhtanov et al. (1995) *Bioconjugate Chemistry* 6:418–426. Acetic anhydride (1.0 ml) was added and the mixture was swirled for 1 h at room temperature and then filtered. The product beads 22 were rinsed with DMF and ethyl acetate and dried under vacuum.

Synthesis of CPG-CDPI$_3$ derivative (23). A suspension of 22 in 15 ml of trifluoroacetic acid was swirled for 1 h at rooom temperature and then filtered. The beads were rinsed with methylene chloride and then with 50 ml of 10% triethylamine in acetonitrile followed by ethyl acetate. The beads were then dried under vacuum.

Activated ester 25 was prepared according to Lukhtanov et al (1997a) supra. A mixture of the glass beads 22 and activated ester 25 (103 mg, 0.22 mmol) was swirled in 6.0 ml of dry pyridine for 18 h at room temperature and then treated with 3.0 ml of acetic anhydride. The mixture was swirled for an additional hour at room temperature and then filtered. The product beads 23 were rinsed with DMF and ethyl acetate and then dried under vacuum.

Synthesis of CPG derivative (15) for oligonucleotide synthesis. A suspension of 23 in 15 ml of trifluoroacetic acid was swirled for 1 h at room temperature and then filtered. The beads were rinsed with methylene chloride and then with 50 ml of 10% triethylamine in acetonitrile followed by ethyl acetate. The beads were dried under vacuum.

A mixture of the beads and 4-nitrophenyl 4-[bis(4-methoxyphenyl)phenyl-methoxy]butanoate (200 mg, 0.378 mmol) was swirled in 6.0 ml of dry pyridine for 18 h at room temperature and then treated with 3.0 ml of acetic anhydride. The mixture was swirled for an additional hour at room temperature and then filtered. The product beads 15 were rinsed with DMF and ethyl acetate and then dried under vacuum. Loading of the beads was 16.7 µmol/g.

Example 7

Synthesis of ODN-MGB-LF (11) in Reaction Scheme 6

The CPG-beads 15 prepared as in Example 6 were deprotected with TFA/CH$_2$Cl$_2$ and used for oligonucleotide synthesis under standard conditions. After synthesis of the oligonucleotide was complete, ammonia deprotection yielded the aminopropyl-CDPI$_3$-ODN derivative 16. Reaction of 16 with a reactive fluorophore derivative (e.g., 5) yielded an ODN-MGB-LF conjugate 17.

Example 8

Mismatch Discrimination using ODN-MGB-TO Conjugates

The ability of ODN-MGB-LF conjugates to discriminate between a perfectly-matched hybrid and a single-nucleotide mismatch was tested, using TO as the latent fluorophore portion of the conjugate. Discriminatory ability was expressed as $\Delta T_{max}$, the difference between the $T_{max}$ values for a perfect match and a single-nucleotide mismatch, where $T_{max}$ is the temperature at which the rate of decrease in fluorescence (-dF/dt, indicative of denaturation of hybrid) is maximum.

ODN-MGB-TO conjugates with ODN portions ranging from 10–18 nucleotides in length were hybridized, at a concentration of 1 μM, to an equimolar concentration of either a target ODN containing a perfectly-matched (i.e., fully complementary) sequence or an ODN containing a single-nucleotide mismatch. The perfectly-matched target had the sequence 5'-CTT CTT TTC TTT AAA TTG CC-3' (SEQ ID NO: 8). The mismatched target had the sequence 5'-CTT CTT TTC TTT CAA TTG CC-3' (SEQ ID NO: 9). The position at which the mismatch occurs in the mismatched oligonucleotide is underlined in all oligonucleotide sequences. Hybridization was conducted in 200 mM NaCl, 10 mM Na cacodylate, 1 mM EDTA, pH 7.2. The hybridization reactions were initially incubated for 15 minutes at room temperature; then the temperature was increased to 95° C. at a rate of 0.2° C. per second.

Fluorescence measurements were conducted on 7 μl of each hybrid, in an Idaho Technologies LC-24 Light Cycler according to the manufacturer's instructions. Fluorescence was continuously monitored at 560 nm and the results are shown in Table 3.

in real-time PCR using ODN-MGB-LF conjugates. See Wittwer et al. (1997) supra for a description of real-time PCR.

Real-time PCR with fluorescent monitoring was performed in an Idaho Technologies LC-24 Light Cycler. Each reaction mixture contained: 40 mM NaCl, 20 mM Tris-HCl, 5 mM MgCl$_2$, 0.05% bovine serum albumin, 125 μM each dNTP, 0.5 μM each primer (including fluorescent primer), 0.1 ng/10 μL template and 0.5 U/10 μL Taq Polymerase. Cycling conditions for this experiment were 40–50 cycles of 1 sec at 95° C., then 30 sec at the annealing/extension temperature of 71° C.

The template was the 4518 bp pBK-CMV phagemid (Stratagene; Alting-Mees, et al. (1992) Strategies 5:58–61. The template contained a LacZ gene insert (ATG at position 1183, TAA at 799) in which the region between nucleotides 1060 and 1083 was substituted with either the matched target sequence 5'-TCT TTC TTC TTT TCT TTA AAT TGC CC-3' (SEQ ID NO: 15) or the mismatched target sequence 5'-TCT TTC TTC TTT TCT TTC AAT-3' (SEQ ID NO: 16).

The following primers were chosen to produce a 42 bp amplicon. The forward primer was 5'-AACCCGCGGCCGCTCTA-3' (SEQ ID NO: 17). Two reverse primers, both containing a LF, were used. The first, which also contained a MGB, was 5'-TO-MGB-CAATT TAAAGAAAAGAAG-3' (SEQ ID NO: 18). The second, which lacked a MGB, was 5'-TO-CAATT TAAAGAAAAGAAG-3' (SEQ ID NO: 19).

Figure 6:
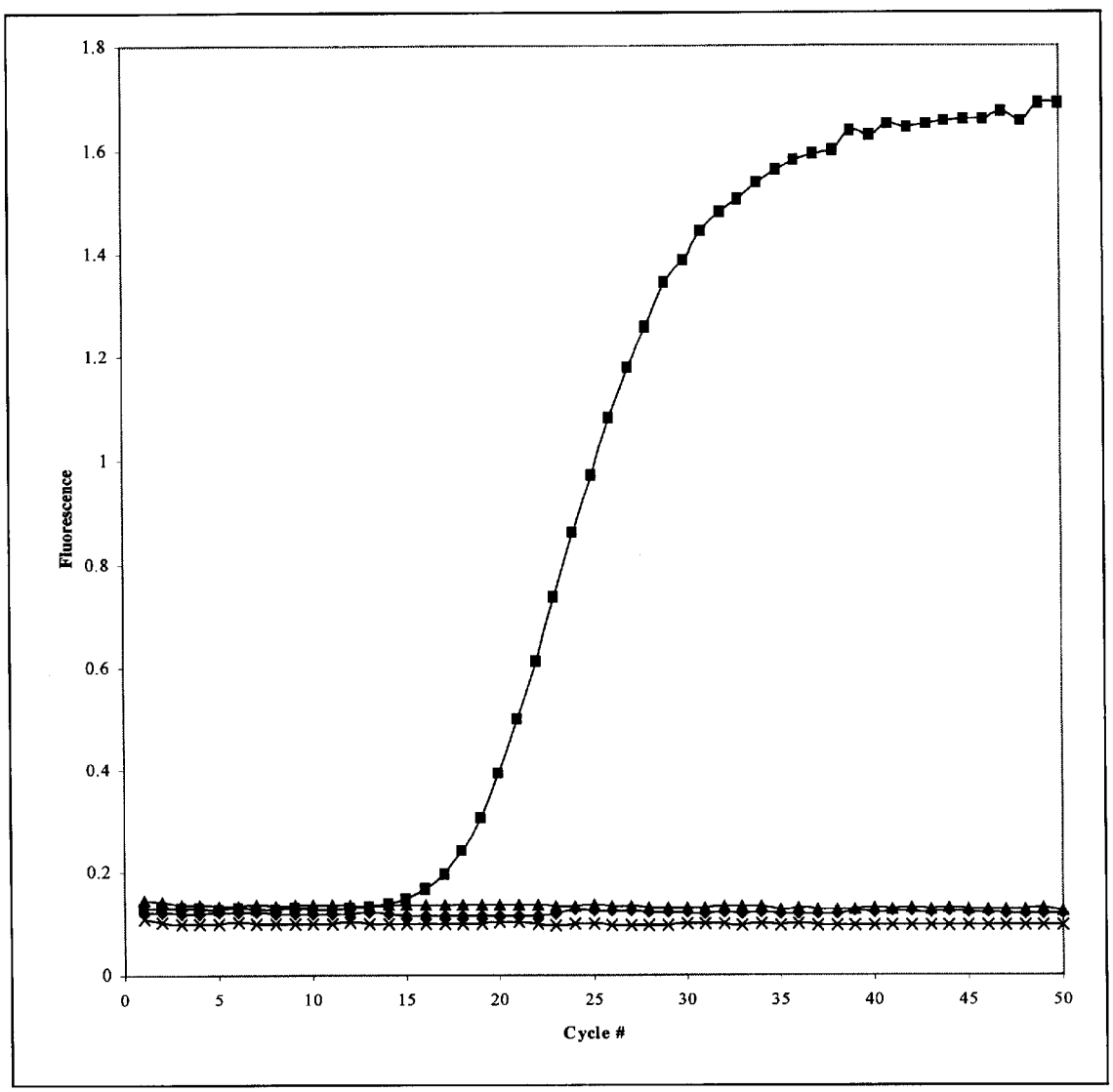
FIG. 6. Single-nucleotide mismatch discrimination by real-time PCR using ODN-MGB-TO conjugates as primers. Symbols are as follows: diamonds: matched primer-TO conjugate (no MGB); squares: matched primer-MGB-TO conjugate; triangles: mismatched primer-MGB-TO conjugate; X: matched primer-MGB-TO conjugate, no template. See Example 9 for details.

FIG. 6 shows fluorescence as a function of cycle number for the ODN-MGB-TO conjugate used as a PCR primer for a perfectly-matched vs. a single-base mismatched primer binding sequence. A strong fluorescence output is observed for the template with the perfectly-matched sequence;

TABLE 3

Mismatch discrimination using ODN-MGB-LF conjugates

| ODN-MGB-LF Conjugate | SEQ ID NO | Length | $T_{max}$ of match | $T_{max}$ of mismatch | $\Delta T_{max}$ |
| --- | --- | --- | --- | --- | --- |
| 5'-TO-MGB-CAATTTAAAGAAAAGAAG | 10 | 18 | 65° C. | 55° C. | 10° C. |
| 5'-TO-MGB-CAATTTAAAGAAAAGA | 11 | 16 | 61° C. | 48.5° C. | 12.5° C. |
| 5'-TO-MGB-CAATTTAAAGAAAA | 12 | 14 | 58° C. | 42° C. | 16° C. |
| 5'-TO-MGB-CAATTTAAAGA | 13 | 12 | 54° C. | 35° C. | 19° C. |
| 5'-TO-MGB-CAATTTAAAG | 14 | 10 | 48° C. | * | |

*duplexes not detected

These results indicate that ODN-MGB-LF conjugates are able to discriminate between a perfectly-matched hybrid and a hybrid containing a single-nucleotide mismatch. Discrimination is achieved for sequences as short as 10 nucleotides.

Example 9

ODN-MGB-fluorophore Conjugates as Primers in Real-time PCR

This example demonstrates that ODN-MGB-LF conjugates are useful as primers in real-time PCR assays, and that single-nucleotide mismatch discrimination can be achieved however, only background fluorescence is observed for the template with the single-base mismatch. FIG. 6 also shows that a TO-conjugated, perfectly-matched primer lacking a MGB yields only background fluorescence in this assay, confirming the beneficial effect of a MGB moiety on hybridization-triggered fluorescence.

Although the foregoing invention has been described in some detail by way of illustration and example for purposes of clarity of understanding, it will be apparent to those skilled in the art that various changes and modifications can be practiced without departing from the spirit of the invention. Therefore the foregoing descriptions and examples should not be construed as limiting the scope of the invention.

What is claimed is:

1. A composition comprising:
   (a) an oligonucleotide (ODN), wherein the oligonucleotide comprises a plurality of nucleotides, a 3' end and a 5' end;
   (b) a minor groove binder (MGB), wherein the minor groove binder is a radical of a molecule having a molecular weight of approximately 150 to approximately 5000 Daltons which molecule binds in a non-intercalating manner into the minor groove of non-single-stranded DNA, RNA or hybrids thereof with an association constant greater than approximately $10^3 M^{-1}$; and
   (c) a latent fluorophore (LF); wherein the latent fluorophore is a radical of a molecule having a molecular weight of approximately 150 to approximately 5000 Daltons which binds in an intercalating manner into non-single-stranded DNA, RNA or hybrids thereof, or alternatively lies in the minor groove, or in another manner is oriented to the DNA molecule by the minor groove binder moiety so that it becomes fluorescent or its fluorescence properties are changed in a detectable way; wherein the composition is a covalently bound oligonucleotide, minor groove binder, latent fluorophore combination having a first linking group and a second linking group.

2. The composition of claim 1, wherein the minor groove binder moiety is covalently linked to the 5' end of the oligonucleotide.

3. The composition of claim 1, wherein the minor groove binder moiety is covalently linked to the 3' end of the oligonucleotide.

4. The composition of claim 1, wherein the minor groove binder moiety is covalently linked to the oligonucleotide at one or more of the nucleotide units.

5. The composition of claim 1, wherein the first linking group comprises a chain having a backbone of no more than about 100 atoms.

6. The composition of claim 1, wherein the second linking group comprises a chain having a backbone of no more than about 50 atoms.

7. The composition of claim 1, wherein the composition does not exhibit substantial fluorescence.

8. The composition of claim 1, wherein the composition does not exhibit detectable fluorescence emission at a particular wavelength.

9. The composition of claim 8, wherein fluorescence emission is increased at the particular wavelength after hybridization of the oligonucleotide to a target sequence.

10. The composition of claim 1, wherein the fluorescence emission maximum shifts from a first wavelength to a second wavelength after hybridization of the oligonucleotide to a target sequence.

11. The composition of claim 1, wherein the oligonucleotide comprises one or more nucleotide analogues.

12. The composition of claim 11, wherein the oligonucleotide is a PNA/DNA chimera, wherein PNA is a polyamide (peptide) nucleic acid.

13. The composition of claim 11, wherein inosine is substituted for guanosine.

14. The composition of claim 11, wherein the oligonucleotide comprises one or more pyrazolopyrimidine nucleotide residues.

15. The composition of claim 14, wherein 6-amino-1H-pyrazolo[3,4-d]pyrimidin-4(5H)-one is substituted for guanine.

16. The composition of claim 14, wherein 4-amino-1H-pyrazolo[3,4-d]pyrimidine is substituted for adenine.

17. The composition of claim 14, wherein 1H-pyrazolo[3,4-d]pyrimidin-4(5H)-6(7H)-dione is substituted for adenine.

18. A method for detecting a target sequence in a polynucleotide, wherein the method comprises:
   (a) combining a composition according to claim 1 with a sample containing a polynucleotide, wherein the oligonucleotide portion of the composition comprises a sequence which hybridizes to the target sequence, to form a hybridization mixture;
   (b) incubating the hybridization mixture under conditions which yield specific hybridization; and
   (c) thereafter measuring fluorescence of the hybridization mixture, wherein fluorescence is indicative of the presence of the target sequence.

19. The method according to claim 18, wherein the polynucleotide is in a sample comprising a plurality of other polynucleotides having different sequences.

20. The method according to claim 18, wherein the sample comprises a signal amplification hybridization reaction.

21. The method according to claim 18, wherein a plurality of target sequences are detected; wherein, for each target sequence, there is a unique ODN-MGB-LF comprising an ODN portion that is complementary to the target sequence and a LF whose fluorescence is distinguishable from that of other LFs conjugated to ODNs complementary to different target sequences.

22. The method according to claim 18, wherein the composition of step (a) is the ODN-MGB-LF of claim 36.

23. A method for detecting a target sequence in a polynucleotide, wherein the polynucleotide is present in a mixture of other polynucleotides, and wherein one or more of the other polynucleotides in the mixture comprise sequences that are related but not identical to the target sequence, the method comprising the steps of:
   (a) contacting the mixture of polynucleotides with a composition according to claim 1, wherein the composition forms a stable hybrid only with said target sequence that is perfectly complementary to the oligonucleotide portion of the composition and wherein the composition does not form a stable hybrid with any of the related sequences; and
   (b) measuring fluorescence, wherein fluorescence is indicative of the presence of the target sequence.

24. The method according to claim 23, wherein one or more of the related sequences has a single-nucleotide mismatch with respect to the ODN portion of the composition.

25. The method according to claim 23, wherein the composition of step (a) is the ODN-MGB-LF of claim 36.

26. A method for detecting one or more sequences related to a target sequence, wherein the one or more related sequences are present in a sample of polynucleotides, the method comprising:
   (a) contacting the sample with a composition according to claim 1, wherein the oligonucleotide portion of the composition has a sequence that is complementary to the target sequence, and wherein the composition forms stable hybrids with the related sequences; and
   (b) measuring fluorescence, wherein fluorescence is indicative of the presence of the one or more related sequences.

27. The method according to claim 26, wherein the composition of step (a) is the ODN-MGB-LF of claim 36.

28. A method for primer extension, wherein the method comprises the steps of:

(a) providing a sample containing a target sequence;
(b) providing one or more oligonucleotide primers, wherein each primer is complementary to a region of the target sequence;
(c) providing a polymerizing enzyme and nucleotide substrates; and
(d) incubating the sample, the oligonucleotide primers, the enzyme and the substrates under conditions favorable for polymerization;
wherein at least one of the primers comprises a ODN-MGB-LF conjugate according to claim 1.

29. The method according to claim 28, wherein the products of polymerization are detected in real time.

30. The method according to claim 28, wherein the composition of step (d) is the ODN-MGB-LF of claim 36.

31. A ODN-MGB-LF according to claim 1 that is immobilized on a solid support.

32. A method for detecting a target sequence, wherein the method comprises:
   (a) immobilizing a ODN-MGB-LF according to claim 1 at an address on a solid support, wherein the ODN is complementary to the target sequence;
   (b) exposing the support to a solution potentially containing the target sequence under conditions favorable to hybridization; and
   (c) thereafter measuring fluorescence of the support, wherein fluorescence at the address is indicative of the presence of the target sequence in the solution.

33. The method according to claim 32, wherein a plurality of ODN-MGB-LFs, having different sequences in their ODN portions, are immobilized at distinct addresses on the support in an ordered array.

34. A kit for hybridization analysis, wherein the kit comprises a composition according to claim 1.

35. The composition of claim 1, wherein the LF is covalently attached to the ODN through said first linking group and the MGB is attached to the LF through said second linking group.

36. The composition of claim 35, wherein the third linking group comprises a chain having a backbone of no more than about 50 atoms.

37. The composition of claim 35, wherein the fourth linking group comprises a chain having a backbone of no more than about 50 atoms.

38. The composition of claim 1, wherein the MGB is covalently attached to the ODN through said first linking group and the MGB is attached to the LF through said second linking group.

39. A composition comprising:

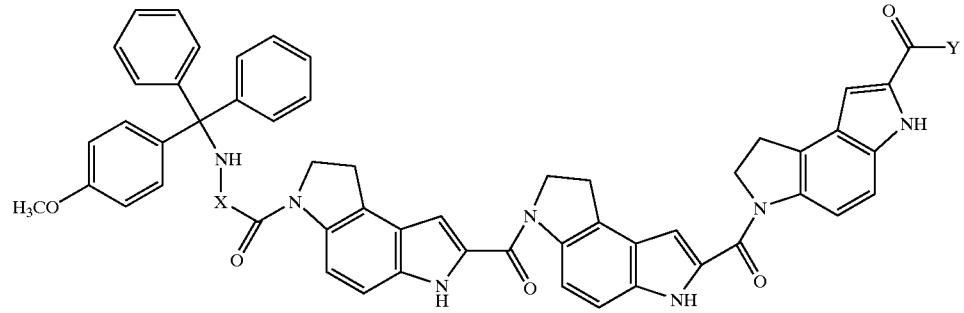

wherein X has a backbone chain length between 0 and 48 atoms long, wherein the backbone contains atoms selected from C, N, O and S, and wherein the backbone optionally contains one or more of —NH—, —O—, —NH—C(=O)—, —C=(O)—NH—, —NH—C(=O)—NH—, —NH—C(=S)—NH—, —SO₂—, —SO₂—NH—, —S— or —S—S— groups;
and wherein Y is a leaving group.

40. The compound of claim 39, wherein the leaving group forms part of an activated ester.

41. The compound of claim 40, wherein the activated ester is selected from the group consisting of hydroxysulfosuccinimide esters, hydroxysuccininimde esters, tetrafluorophenyl esters and anhydrides.

42. A method for the synthesis of a ODN-MGB-LF conjugate, wherein the method comprises:
   (a) treating the composition of claim 39 with an acid; and
   (b) reacting the product of step (a) with an amino-tailed ODN and with a LF, wherein the LF comprises a linking group which terminates in a reactive group.

43. A composition comprising:

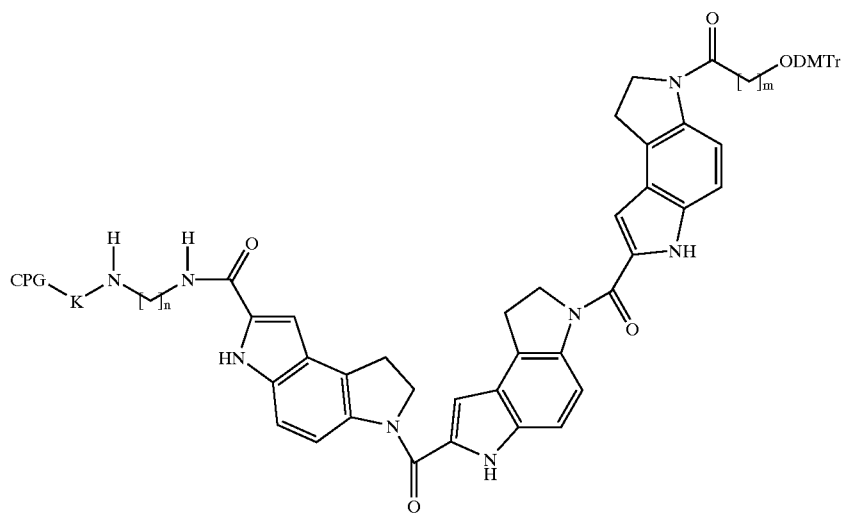

wherein K is a cleavable linker;

m is between 1 and 99; and n is between 1 and 47.

44. The composition of claim 43, wherein K is

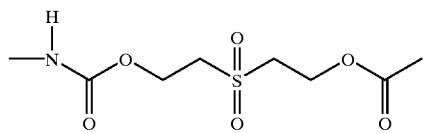

45. A method for the synthesis of a ODN-MGB-LF conjugate, wherein the method comprises:

(a) removing the DMTr group from the composition of claim 43;

(b) using the product of step (a) for oligonucleotide synthesis to generate a CPG-MGB-ODN;

(c) removing the MGB-ODN of step (b) from the CPG by cleavage at the cleavable linker K; and (d) reacting the product of step (c) with a LF, wherein the LF comprises a linking group which terminates in a reactive group, to produce a ODN-MGB-LF.

* * * * *

SEQUENCE LISTING

<160> NUMBER OF SEQ ID NOS: 19

<210> SEQ ID NO 1
<211> LENGTH: 12
<212> TYPE: DNA
<213> ORGANISM: Artificial Sequence
<220> FEATURE:
<223> OTHER INFORMATION: synthetic construct

<400> SEQUENCE: 1
caatttaaag aa                                                        12

<210> SEQ ID NO 2
<211> LENGTH: 12
<212> TYPE: DNA
<213> ORGANISM: Artificial Sequence
<220> FEATURE:
<223> OTHER INFORMATION: synthetic construct

<400> SEQUENCE: 2
ttcccgagcg gc                                                        12

<210> SEQ ID NO 3
<211> LENGTH: 18
<212> TYPE: DNA
<213> ORGANISM: Artificial Sequence
<220> FEATURE:
<223> OTHER INFORMATION: synthetic construct

<400> SEQUENCE: 3
caatttaaag aaaagaag                                                  18

<210> SEQ ID NO 4
<211> LENGTH: 17
<212> TYPE: DNA
<213> ORGANISM: Artificial Sequence
<220> FEATURE:
<223> OTHER INFORMATION: synthetic construct

<400> SEQUENCE: 4
tttcttaaaa cgaattt                                                   17

<210> SEQ ID NO 5
<211> LENGTH: 17
<212> TYPE: DNA
<213> ORGANISM: Artificial Sequence
<220> FEATURE:
<223> OTHER INFORMATION: synthetic construct

<400> SEQUENCE: 5
tttcttaaca cgaattt                                                   17

<210> SEQ ID NO 6
<211> LENGTH: 10
<212> TYPE: DNA
<213> ORGANISM: Artificial Sequence
<220> FEATURE:
<223> OTHER INFORMATION: synthetic construct

<400> SEQUENCE: 6
gaagttgctt                                                           10

<210> SEQ ID NO 7
<211> LENGTH: 11

```
<212> TYPE: DNA
<213> ORGANISM: Artificial Sequence
<220> FEATURE:
<223> OTHER INFORMATION: synthetic construct

<400> SEQUENCE: 7
gaattttgct t                                                          11

<210> SEQ ID NO 8
<211> LENGTH: 20
<212> TYPE: DNA
<213> ORGANISM: Artificial Sequence
<220> FEATURE:
<223> OTHER INFORMATION: synthetic construct

<400> SEQUENCE: 8
cttcttttct ttaaattgcc                                                 20

<210> SEQ ID NO 9
<211> LENGTH: 20
<212> TYPE: DNA
<213> ORGANISM: Artificial Sequence
<220> FEATURE:
<223> OTHER INFORMATION: synthetic construct

<400> SEQUENCE: 9
cttcttttct ttcaattgcc                                                 20

<210> SEQ ID NO 10
<211> LENGTH: 18
<212> TYPE: DNA
<213> ORGANISM: Artificial Sequence
<220> FEATURE:
<223> OTHER INFORMATION: synthetic construct

<400> SEQUENCE: 10
caatttaaag aaaagaag                                                   18

<210> SEQ ID NO 11
<211> LENGTH: 16
<212> TYPE: DNA
<213> ORGANISM: Artificial Sequence
<220> FEATURE:
<223> OTHER INFORMATION: synthetic construct

<400> SEQUENCE: 11
caatttaaag aaaaga                                                     16

<210> SEQ ID NO 12
<211> LENGTH: 14
<212> TYPE: DNA
<213> ORGANISM: Artificial Sequence
<220> FEATURE:
<223> OTHER INFORMATION: synthetic construct

<400> SEQUENCE: 12
caatttaaag aaaa                                                       14

<210> SEQ ID NO 13
<211> LENGTH: 11
<212> TYPE: DNA
<213> ORGANISM: Artificial Sequence
<220> FEATURE:
<223> OTHER INFORMATION: synthetic construct

<400> SEQUENCE: 13
```
caatttaaag a                                                                    11

<210> SEQ ID NO 14
<211> LENGTH: 10
<212> TYPE: DNA
<213> ORGANISM: Artificial Sequence
<220> FEATURE:
<223> OTHER INFORMATION: synthetic construct

<400> SEQUENCE: 14
caatttaaag                                                                      10

<210> SEQ ID NO 15
<211> LENGTH: 26
<212> TYPE: DNA
<213> ORGANISM: Artificial Sequence
<220> FEATURE:
<223> OTHER INFORMATION: synthetic construct

<400> SEQUENCE: 15
tctttcttct tttctttaaa ttgccc                                                    26

<210> SEQ ID NO 16
<211> LENGTH: 21
<212> TYPE: DNA
<213> ORGANISM: Artificial Sequence
<220> FEATURE:
<223> OTHER INFORMATION: synthetic construct

<400> SEQUENCE: 16
tctttcttct tttctttcaa t                                                         21

<210> SEQ ID NO 17
<211> LENGTH: 17
<212> TYPE: DNA
<213> ORGANISM: Artificial Sequence
<220> FEATURE:
<223> OTHER INFORMATION: synthetic construct

<400> SEQUENCE: 17
aacccgcggc cgctcta                                                              17

<210> SEQ ID NO 18
<211> LENGTH: 18
<212> TYPE: DNA
<213> ORGANISM: Artificial Sequence
<220> FEATURE:
<223> OTHER INFORMATION: synthetic construct

<400> SEQUENCE: 18
caatttaaag aaaagaag                                                             18

<210> SEQ ID NO 19
<211> LENGTH: 18
<212> TYPE: DNA
<213> ORGANISM: Artificial Sequence
<220> FEATURE:
<223> OTHER INFORMATION: synthetic construct

<400> SEQUENCE: 19
caatttaaag aaaagaag                                                             18